US008431611B2

(12) United States Patent
Brando et al.

(10) Patent No.: US 8,431,611 B2
(45) Date of Patent: Apr. 30, 2013

(54) ARTEMISININ DERIVATIVES

(75) Inventors: Lorraine V. Brando, Baltimore, MD (US); Gary H. Posner, Baltimore, MD (US); John G. D'Angelo, Lindenhurst, NY (US); Robert H. Yolken, Baltimore, MD (US); Christopher P. Hencken, Baltimore, MD (US); Lauren Woodard, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 620 days.

(21) Appl. No.: 12/445,499

(22) PCT Filed: Oct. 19, 2007

(86) PCT No.: PCT/US2007/081907
§ 371 (c)(1),
(2), (4) Date: Dec. 17, 2009

(87) PCT Pub. No.: WO2008/127381
PCT Pub. Date: Oct. 23, 2008

(65) Prior Publication Data
US 2010/0093651 A1    Apr. 15, 2010

Related U.S. Application Data

(60) Provisional application No. 60/853,386, filed on Oct. 20, 2006, provisional application No. 60/936,619, filed on Jun. 21, 2007.

(51) Int. Cl.
*A01N 43/02*    (2006.01)
*A61K 31/335*   (2006.01)

(52) U.S. Cl.
USPC .......................... 514/450; 514/183; 514/449

(58) Field of Classification Search .................. None
See application file for complete search history.

(56) References Cited

U.S. PATENT DOCUMENTS

| | | | |
|---|---|---|---|
| 5,225,562 A | 7/1993 | McChesney et al. | |
| 6,156,790 A | 12/2000 | Posner et al. | |
| 6,160,004 A * | 12/2000 | Posner et al. | 514/450 |
| 2006/0074251 A1 | 4/2006 | Jung | |

FOREIGN PATENT DOCUMENTS

| | | |
|---|---|---|
| EP | 1 655 302 A2 | 5/2006 |
| EP | 1 655 302 A3 | 5/2006 |
| WO | WO 03/076446 A1 | 9/2003 |

OTHER PUBLICATIONS

Jeyadevan et al. J. Med. Chem. (2004), vol. 47, pp. 1290-1298.*
Jones-Brando et al., "In vitro inhibition of *Toxoplasma gondii* by four new derivatives of artemisinin", *Antimicrob. Agents Chemother.*, 50(12):4206-4208 (2006), Epub Oct. 23, 2006.
Jung et al., "Antiangiogenic activity of deoxoartemisinin derivatives on chorioallantoic membrane", *Bioorg. Med. Chem. Lett.*, 16(5):1227-1230 (2006), Epub Dec. 27, 2005.
Jung et al., "Antitumor activity of novel deoxoartemisinin monomers, dimers, and trimer", *J. Med. Chem.*, 46(6):987-94 (2003).
Katritzky et al., "Antimalarial activity: a QSAR modeling using CODESSA PRO software", *Bioorg. Med. Chem.*, 14(7):2333-57 (2006), Epub Jan. 19, 2006.
O'Dowd et al., "Antimalarial Artemisinin Analogs. Synthesis via Chemoselective C-C bond Formation and Preliminary Biological Evaluation", *Tetrahedron*, 55:3625-3636 (1999).
Bachmann, S., et al. "Psychopathology in First-Episode Schizophrenia and Antibodies to *Toxoplasma gondii*, " *Psychopathol*, 2005, pp. 87-90, vol. 38, No. 2.
Berens, R. L., et al, "Selection and characterization of *Toxoplasma gondii* mutants resistant to artemisinin," *The Journal of Infectious Diseases*, Apr. 1998, pp. 1128-1131, vol. 177.
Berge, S. M. at al., "Pharmaceutical Salts," *Journal of Pharmaceutical Science*, Jan. 1977, pp. 1-19, vol. 66, No. 1.
Brossi, A., B. et al., "Arteether, a new antimalarial drug: Synthesis and antimalarial properties," *Journal of Medicinal Chemistry*, Mar. 1988, pp. 645-650, vol. 31, No. 3.
Chang, H R., et al., "In Vitro Effects of Three New 1,2,4-Trioxanes (Pentatroxane, Thiahexatroxane, and Hexatroxanone) on *Toxoplasma gondii*," *Antimicrobial Agents and Chemotherapy*, Oct. 1989, pp. 1748-1752, vol. 33, No. 10.
Dobrowolski, J, M., et al., "Toxoplasma Invasion of Mammalian Cells is Powered by the Actin Cytoskeleton of the Parasite," *Cell*, Mar. 22, 1996, pp. 933-939, vol. 84, No. 6.
Gennaro, A. R. ed,, "Remington: The Science and Practice of Pharmacy, 20th editition," Lippincott Williams and Wilkins, 2000, Baltimore, MD.
Greene, T. W. et al, "Protective Groups in Organic Synthesis, 3rd edition," John Wiley & Sons (1999).
Holfels, E., J. et al., "In vitro Effects of Artemisinin Ether, Cycloguanil Hydrochloride (Alone and in Combination with Sulfadiazine), Quinine Sulfate, Mefloquine, Primaquine Phosphate, Trifluoperazine Hydrochloride, and Verapamil on *Toxoplasma gondii*," *Antimicrobial Agents and Chemotherapy*, Jun. 1994 pp. 1392-1396, vol. 38, No. 6.
Huynh, M.-H. et al., "Rapid Invasion of Host Cells by *Toxoplasma* Requires Secretion of the MIC2-M2AP Adhesive Protein Complex," *The European Molecular Biology Organization Journal*, May 2003, pp. 2082-2090. vol. 22, No. 9.
Jones-Brando, L., et al., In Vitro Inhibition of *Toxoplasma Gondii* by Four New Derivatives of Artemisinin. *Antimicrobial Agents and Chemotherapy*, Dec. 2006, pp, 4206-4208, vol. 50, No. 12.

(Continued)

*Primary Examiner* — Patrick Lewis
(74) *Attorney, Agent, or Firm* — DLA Piper LLP (US)

(57) ABSTRACT

This disclosure provides improved derivatives of artemisinin; pharmaceutical compositions containing these compounds; methods for preparing these compounds and compositions; methods of using these compounds and compositions for preventing, controlling or treating infectious diseases including but not limited to parasitic infectious diseases such as *T. gondii* infection, trypanosome parasite infection, plasmodia parasite infection, and cryptosporidium parasite infection; methods for preventing, controlling or treating toxoplasma infection; and methods for treating psychiatric disorders associated with toxoplasma infection including but not limited to schizophrenia using the disclosed compounds and compositions alone or in combination with one or more antipsychotic drugs.

20 Claims, 2 Drawing Sheets

OTHER PUBLICATIONS

Jones-Brando. L. et al., "Drugs Used in the Treatment of Schizophrenia and Bipolar Disorder Inhibit the Replication of *Toxoplasma gondii*," *Schizophrenia Research*, Aug. 1, 2003, pp. 237-244, vol. 62, Issue 3.

Lin A, J. et al., "Antimalarial Activity of New Water-Soluble Dihydroartemisinin Derivatives," *The Journal of Medicinal Chemistry*, Nov. 30, 1987, pp. 2147-2150, vol. 30, No. 11.

O'Neill, P. M. et al., "A Medicinal Chemistry Perspective on Artemisinin and Related Endoperoxides," *The Journal of Medicinal Chemistry*, Jun. 3, 2004, pp. 2945-2964, vol. 47, No. 12.

Ou-Yang, K. et al., "Inhibition of Growth of *Toxoplasma gondii* by Qinghaosu and Derivatives," *Antimicrobial Agents and Chemotherapy*, Oct. 1990, pp. 1961-1965, vol. 34, No. 10.

Silverman, J.A, et al., "Characterization of Anti-Toxoplasma Activity of SDZ 215-918, a Cyclosporin Derivative Lacking Immunosuppressive and Peptidyl-Prolyl-Isomerase-Inhibiting Activity: Possible Role of a P Glycoprotein in *Toxoplasma* Physiology," *Antimicrobial Agents and Chemotherapy*, Sep. 1997, pp. 1859-1866, vol. 41, No. 9.

St. Georgiev, V., "Management of Toxoplasmosis," *Drugs*, Aug. 1994, pp. 179-188, vol. 48, No. 2.

Tenter, A. M. et al., "*Toxoplasma gondii*: From Animals to Humans," *International Journal for Parasitology*, Nov. 2000, pp. 1217-1258, vol, 30, Issue 12-13.

Torrey, E. F., et al., "Antibodies to *Toxopiasma gondii* in Patients with Schizophrenia: A Meta-Analysis," *Schizophrenia Bulletin*, May 2007 (online Nov. 3, 2006), pp. 729-736. vol. 33, No. 3.

Yolken, R. H, et al., Antibodies to *Toxoplasma gondii* in Individuals with First-Episode Schizophrenia. *Clinical Infectious Diseases Brief Reports*, Mar. 1, 2001, pp. 842-844, vol. 32, No. 5.

* cited by examiner

ARTEMISININ DERIVATIVES

This application is a 35 USC §371 National Stage application of International Application No. PCT/US2007/081907 filed Oct. 19, 2007, now pending; which claims the benefit under 35 USC §119(e) to U.S. Application Ser. No. 60/936,619 filed Jun. 21, 2007, now abandoned and to U.S. Application Ser. No. 60/853,386 filed Oct. 20, 2006, now abandoned. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH AND DEVELOPMENT

This invention was made with government support under Grant No. AI 34885 awarded by the National Institutes of Health. The government has certain rights in the invention.

FIELD OF THE DISCLOSURE

This disclosure relates to the field of novel derivatives of Artemisinin which are useful for preventing, treating and controlling infections, including but not limited to toxoplasmic infection, and psychiatric conditions associated with toxoplasmic infection.

BACKGROUND OF THE DISCLOSURE

Toxoplasma gondii (T. gondii) is an apicomplexan protozoan of world-wide medical importance. Humans are infected by T. gondii through contact with feces from infected cats, by the consumption of undercooked meat from infected animals, or by transmission from infected mother to fetus. This parasite can cause systemic infection and widespread organ damage in immunocompromised individuals and neonates. Infection of immunocompetent adults can result in fever and adenopathy (15). Serological studies indicate that T. gondii could be associated with chronic neuropsychiatric diseases or behavioral abnormalities in some populations (1, 17).

Available medications for the prevention and treatment of toxoplasma infection show limited efficacy and have substantial side effects (6). Published studies have indicated that the naturally occurring 1,2,4-trioxane artemisinin and artemisinin derivatives such as artemether, originally developed for the treatment of malaria, have the ability to inhibit toxoplasma replication in vitro (2, 4, 7, 13). While these trioxanes have a number of advantages in terms of rapid action and low levels of toxicity, they are limited in terms of absorption, bioavailability, and short half-life (i.e., easy hydrolysis into toxic dihydroartemisinin) (11, 12). Thus, what is needed are improved derivatives of artemisinin having not only rapid action and low levels of toxicity, but also better absorption, bioavailability, and longer half-lives for inhibiting the replication of T. gondii.

BRIEF SUMMARY OF THE DISCLOSURE

This disclosure provides improved derivatives of artemisinin; pharamaceutical compositions containing these compounds; methods for preparing these compounds and compositions; methods of using these compounds and compositions for preventing, controlling or treating infectious diseases including but not limited to parasitic infectious diseases such as T. gondii infection, trypanosome parasite infection, plasmodia parasite infection, and cryptosporidium parasite infection; methods for preventing, controlling or treating toxoplasma infection; and methods for treating psychiatric disorders associated with toxoplasma infection including but not limited to schizophrenia using the disclosed compounds and compositions alone or in combination with one or more antipsychotic drugs.

Thus, in one aspect, the disclosure provides compounds having formula I:

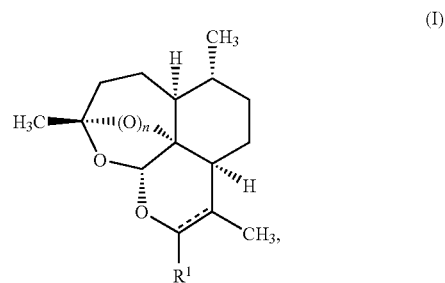

or an enantiomer, diastereomer, racemate or pharmaceutically acceptable salt or solvate thereof, wherein:

------ is a single or a double bond;

n is independently an integer from 1 to 2;

$R^1$ includes but is not limited to substituted or unsubstituted alkyl, substituted or unsubstituted aryl, substituted or unsubstituted arylalkyl, substituted or unsubstituted heteroaryl, substituted or unsubstituted heteroarylalkyl, —$(CH_2)_jR^2$, —$(CH_2)_jO(CH_2)_kR^2$, —$(CH_2)_jC(O)(CH_2)_kR^2$, —$(CH_2)_jC(O)(CH_2)_kR^2$, —$(CH_2)_jC(O)O(CH_2)_kR^2$, —$(CH_2)_jNR^3R^4$, —$(CH_2)_jC(O)(CH_2)_kNR^3R^4$, —$(CH_2)_jNR^5C(O)(CH_2)_kR^2$, —$(CH_2)_jC(O)(CH_2)_kNR^3R^4$, —$(CH_2)_jNR^5C(O)(CH_2)_kOR^2$, —$(CH_2)_jNR^5C(O)(CH_2)_kNR^3R^4$, wherein each j and each k is independently an integer from 0 to 6; and m is independently an integer from 0 to 2;

$R^2$ includes but is not limited to hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, substituted or unsubstituted (aryl or heteroaryl)-X-(aryl or heteroaryl) wherein X is O, S, NH or $N(C_1-C_6)$alkyl, cholesterol, or a substituted or unsubstituted monosaccharide, and wherein each $R^2$ is optionally independently substituted with 1 to 5 $R^{10}$ groups;

$R^3$, $R^4$, and $R^5$ includes but are not limited to hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^3$, $R^4$, and $R^5$, are each optionally independently substituted with 1 to 5 $R^{10}$ groups, or $R^3$ and $R^4$, together with the N atom to which they are attached, form substituted or unsubstituted heterocycloalkyl, or substituted or unsubstituted heteroaryl, wherein substituted or unsubstituted heterocycloalkyl, and substituted or unsubstituted heteroaryl are each optionally independently substituted with 1 to 5 $R^{10}$ groups, and $R^5$ is as described above; and each $R^{10}$ includes but is not limited to hydrogen, halogen, hydroxyl, amino, aminoalkyl, aminodialkyl, cyano, nitro, alkyl, —O-alkyl, —S-alkyl, perfluoroalkyl, —O-perfluoroalkyl, oxo, acetyl, or -benzyl.

In other aspects, the disclosure provides pharmaceutical compositions, methods of using and methods for preparing compounds having formula I.

DETAILED DESCRIPTION OF THE DISCLOSURE

Figure 1:
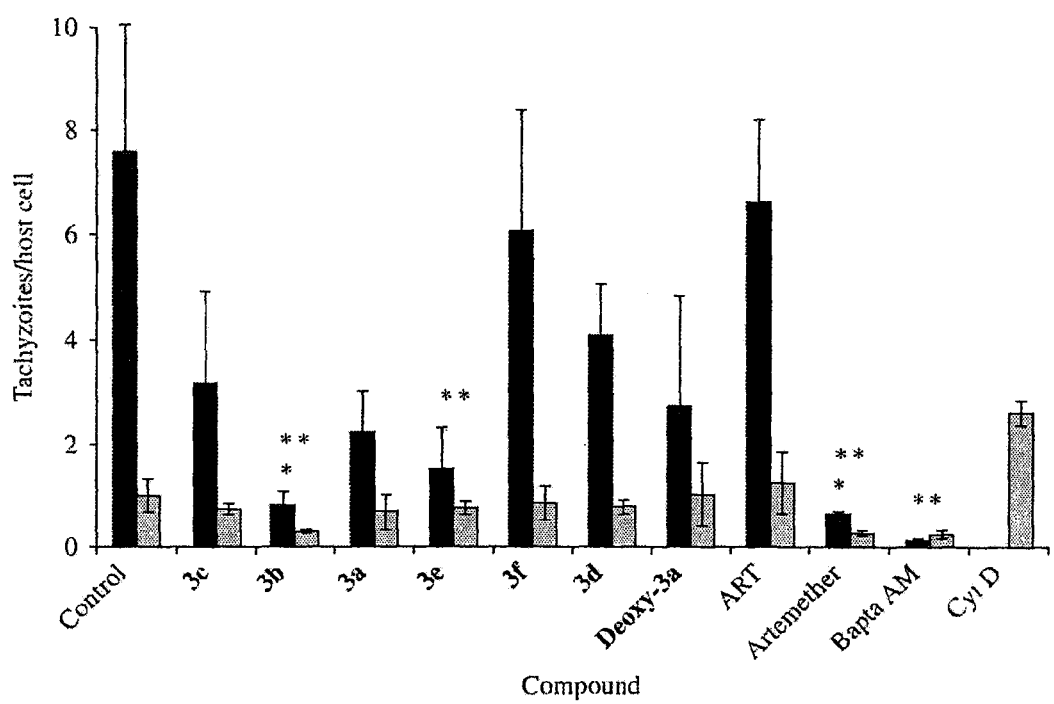
FIG. 1 illustrates the quantification of invasion using red/green assay. Green bars represent internal/penetrated parasites while red bars depict external/attached parasites. Compounds were tested at 10 μg/ml (range 25-34 μM). BAPTA-AM (20 μM) and cytochalasin D (Cyt D, 2 μM) were included as positive controls for inhibition of attachment or penetration, respectively. Data are mean values±SEM of three independent experiments, counting ten random fields for each sample. These data show that with the exception of artemisinin (ART) and derivative 3f, the compounds effectively inhibit the attachment of *T. gondii* tachyzoites to HFF cells. In addition, they moderately inhibit the penetration of the cells. Because the parasites are exposed to the compounds in vitro, i.e. in a test tube outside of the cells, these results suggest that some of the derivatives are active extracellularly as well as intracellularly (see Table 1). It is interesting to note that while deoxy-3a displays little or no efficacy in the growth inhibition assay (Table 1), it is effective in inhibition of attachment.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon group, or combination thereof, which may be fully saturated, mono- or polyunsaturated and can include di- and multivalent groups, having the number of carbon atoms designated (i.e. $C_1$-$C_{10}$ means one to ten carbons). Examples of saturated hydrocarbon groups include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent group derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$.

Similarly, the term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R' or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkyl" or "cycloalkylalkyl" also refers to a 3 to 7 membered cycloalkyl group attached to the remainder of the molecule via an unsubstituted alkylene group. Recitation of a specific number of carbon atoms (e.g. $C_1$-$C_{10}$ cycloalkylalkyl) refers to the number of carbon atoms in the alkylene group.

The term "heterocycloalkyl" or "heterocycloalkylalkyl" also refers to a 3 to 7 membered heterocycloalkyl group attached to the remainder of the molecule via an unsubstituted alkylene group. Recitation of a specific number of carbon atoms (e.g. $C_1$-$C_{10}$ hetero-cycloalkylalkyl) refers to the number of carbon atoms in the alkylene group.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, an aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those groups in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent derivatives) are meant to include both substituted and unsubstituted forms of the indicated group. Preferred substituents for each type of group are provided below.

Substituents for alkyl, heteroalkyl, cycloalkyl, heterocloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such group. R', R", R'" and R'" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R'" and R'" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R'" and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R'" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R′″ are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$— or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium (3H), iodine-125 ($^{125}I$) or carbon-14 ($^{14}C$). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

In addition to salt forms, the present disclosure relates to compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

The terms "treating" or "treatment" in reference to a particular disease includes prevention of the disease.

The structure:

signifies the point of attachment of a moiety "R" to the remainder of the molecule.

The structure: R⌇⌇⌇ signifies mixtures of α- and β-isomers.

Artemisinin Derivatives

In one aspect, the disclosure provides compounds having formula I:

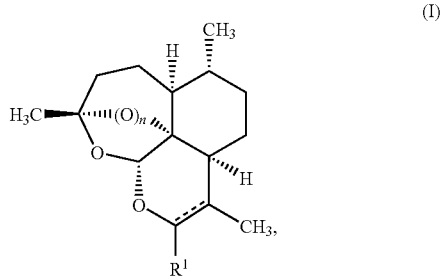

(I)

or an enantiomer, diastereomer, racemate or pharmaceutically acceptable salt or solvate thereof, wherein:

⸺⸺ is a single or a double bond;

n is independently an integer from 1 to 2;

$R^1$ includes but is not limited to substituted or unsubstituted alkyl, substituted or unsubstituted aryl, substituted or unsubstituted arylalkyl, substituted or unsubstituted heteroaryl, substituted or unsubstituted heteroarylalkyl, —$(CH_2)_jR^2$, —$(CH_2)_j$—O—$(CH_2)_kR^2$, —$(CH_2)_jC(O)(CH_2)_kR^2$, —$(CH_2)_jOC(O)(CH_2)_kR^2$, —$(CH_2)_jC(O)O$ $(CH_2)_kR^2$, —$(CH_2)_jNR^3R^4$, —$(CH_2)_jC(O)(CH_2)_kNR^3R^4$, —$(CH_2)_jNR^5C(O)(CH_2)_kR^2$, —$(CH_2)_jOC(O)(CH_2)_k NR^3R^4$, —$(CH_2)_jNR^5C(O)(CH_2)_kOR^2$, or —$(CH_2)_jNR^5C(O)(CH_2)_kNR^3R^4$, wherein each j and each k is independently an integer from 0 to 6; and m is independently an integer from 0 to 2;

$R^2$ includes but is not limited to hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, substituted or unsubstituted (aryl or heteroaryl)-X-(aryl or heteroaryl) wherein X is O, S, NH or N($C_1$-$C_6$)alkyl, cholesterol, or a substituted or unsubstituted monosaccharide, and wherein each $R^2$ is optionally independently substituted with 1 to 5 $R^{10}$ groups;

$R^3$, $R^4$, and $R^5$ includes but are not limited to hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^3$, $R^4$, and $R^5$, are each optionally independently substituted with 1 to 5 $R^{10}$ groups, or $R^3$ and $R^4$, together with the N atom to which they are attached, form substituted or unsubstituted heterocycloalkyl, or substituted or unsubstituted heteroaryl, wherein substituted or unsubstituted heterocycloalkyl, and substituted or unsubstituted heteroaryl are each optionally independently substituted with 1 to 5 $R^{10}$ groups, and $R^5$ is as described above; and each $R^{10}$ includes but is not limited to hydrogen, halogen, hydroxyl, amino, aminoalkyl, aminodialkyl, cyano, nitro, alkyl, —O-alkyl, —S-alkyl, perfluoroalkyl, —O-perfluoroalkyl, oxo, acetyl, or -benzyl.

In another aspect, the disclosure provides compounds having formula I, wherein: $R^1$ includes but is not limited to substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl.

In another aspect, the disclosure provides compounds having formula I, wherein $R^1$ includes but is not limited to —(CH₂)ⱼC(O)(CH₂)ₖR², —(CH₂)ⱼOC(O)(CH₂)ₖR², —(CH₂)ⱼC(O)O(CH₂)ₖR², or —(CH₂)ⱼC(O)(CH₂)ₖNR³R⁴; and R² includes but is not limited to hydrogen, substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl; and R³ and R⁴ includes but are not limited to hydrogen, substituted or unsubstituted alkyl, substituted or unsubstituted phenyl, substituted or unsubstituted benzyl, or R³ and R⁴, together with the N atom to which they are attached, form substituted or unsubstituted pyrrolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl.

In another aspect, the disclosure provides compounds having formula I, wherein:

R¹ includes but is not limited to —C(O)R², —OC(O)R², —C(O)OR², or —C(O)NR³R⁴;

R² includes but is not limited to hydrogen, substituted or unsubstituted alkyl, or substituted or unsubstituted phenyl; and R³ and R⁴ includes but are not limited to hydrogen, or substituted or unsubstituted alkyl.

In another aspect, the disclosure provides compounds having formula I, wherein:

R¹ includes but is not limited to —(CH₂)ⱼC(O)O(CH₂)ₖR²; and

R² includes but is not limited to substituted or unsubstituted glucose, substituted or unsubstituted galactose, substituted or unsubstituted mannose, substituted or unsubstituted fructose.

In another aspect, the disclosure provides compounds having formula I, wherein:

R¹ includes but is not limited to —C(O)OR²; and

R² includes but is not limited to tetraacetyl α-D glucopyranose, tetraacetyl β-D glucopyranose, tetraacetyl α-D galactose, tetraacetyl β-D galactose, tetraacetyl α-D mannose, tetraacetyl β-D mannose, tetraacetyl α-D fructose, or tetraacetyl β-D fructose.

In another aspect, the disclosure provides compounds having formula I, wherein the compound of formula I, has formula II:

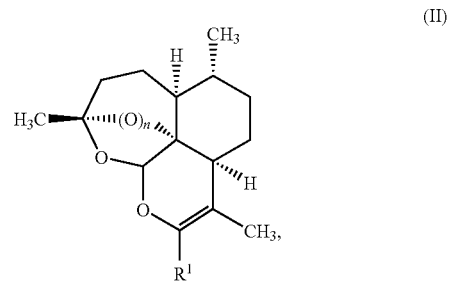

wherein:

R¹ includes but is not limited to substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, —(CH₂)ⱼC(O)(CH₂)ₖR², —(CH₂)ⱼOC(O)(CH₂)ₖR², —(CH₂)ⱼC(O)O(CH₂)ₖR², or —(CH₂)ⱼC(O)(CH₂)ₖNR³R⁴;

R² includes but is not limited to hydrogen, substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted phthalazinyl, substituted or unsubstituted quinazolinyl, or substituted or unsubstituted quinoxalinyl, or substituted or unsubstituted phenyl-NH-phenyl; and $R^3$ and $R^4$ includes but are not limited to hydrogen, substituted or unsubstituted alkyl, substituted or unsubstituted phenyl, substituted or unsubstituted benzyl, or $R^3$ and $R^4$, together with the N atom to which they are attached, form substituted or unsubstituted pyrrolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl.

In another aspect, the disclosure provides compounds having formula II, wherein:

$R^1$ includes but is not limited to —C(O)$R^2$, —OC(O)$R^2$, —C(O)O$R^2$, or —C(O)N$R^3R^4$;

$R^2$ includes but is not limited to hydrogen, substituted or unsubstituted alkyl, or substituted or unsubstituted phenyl; and $R^3$ and $R^4$ includes but are not limited to hydrogen, or substituted or unsubstituted alkyl.

In another aspect, the disclosure provides compounds having formula II, wherein:

$R^1$ includes but is not limited to —(CH$_2$)$_j$C(O)O(CH$_2$)$_k R^2$; and $R^2$ includes but is not limited to substituted or unsubstituted glucose, substituted or unsubstituted galactose, substituted or unsubstituted mannose, substituted or unsubstituted fructose.

In another aspect, the disclosure provides compounds having formula II, wherein:

$R^1$ includes but is not limited to —C(O)O$R^2$; and $R^2$ includes but is not limited to tetraacetyl α-D glucopyranose, tetraacetyl β-D glucopyranose, tetraacetyl α-D galactose, tetraacetyl β-D galactose, tetraacetyl α-D mannose, tetraacetyl β-D mannose, tetraacetyl α-D fructose, or tetraacetyl β-D fructose.

In another aspect, the disclosure provides compounds having formula II, wherein the compound of formula I, has formula III:

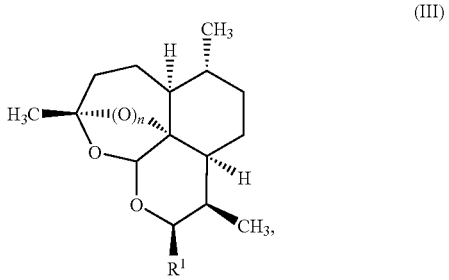

(III)

In another aspect, the disclosure provides compounds having formula III, wherein:

$R^1$ includes but is not limited to substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, —(CH$_2$)$_j$C(O)(CH$_2$)$_k R^2$, —(CH$_2$)$_j$OC(O)(CH$_2$)$_k R^2$, —(CH$_2$)$_j$C(O)O(CH$_2$)$_k R^2$, or —(CH$_2$)$_j$C(O)(CH$_2$)$_k$N$R^3R^4$;

$R^2$ includes but is not limited to hydrogen, substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, or substituted or unsubstituted phenyl-NH-phenyl; and $R^3$ and $R^4$ includes but are not limited to hydrogen, substituted or unsubstituted alkyl, substituted or unsubstituted phenyl, substituted or unsubstituted benzyl, or $R^3$ and $R^4$, together with the N atom to which they are attached, form substituted or unsubstituted pyrrolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl.

In another aspect, the disclosure provides compounds having formula III, wherein:

$R^1$ includes but is not limited to —C(O)$R^2$, —OC(O)$R^2$, —C(O)O$R^2$, or —C(O)N$R^3R^4$;

$R^2$ includes but is not limited to hydrogen, substituted or unsubstituted alkyl, or substituted or unsubstituted phenyl; and $R^3$ and $R^4$ includes but are not limited to hydrogen, or substituted or unsubstituted alkyl.

In another aspect, the disclosure provides compounds having formula II, wherein:

R¹ includes but is not limited to —(CH₂)ⱼC(O)O(CH₂)ₖR²; and

R² includes but is not limited to substituted or unsubstituted glucose, substituted or unsubstituted galactose, substituted or unsubstituted mannose, substituted or unsubstituted fructose.

In another aspect, the disclosure provides compounds having formula III, wherein:

R¹ includes but is not limited to —C(O)OR²; and

R² includes but is not limited to tetraacetyl α-D glucopyranose, tetraacetyl β-D glucopyranose, tetraacetyl α-D galactose, tetraacetyl β-D galactose, tetraacetyl α-D mannose, tetraacetyl β-D mannose, tetraacetyl α-D fructose, or tetraacetyl β-D fructose.

In another aspect, the disclosure provides compounds having formula:

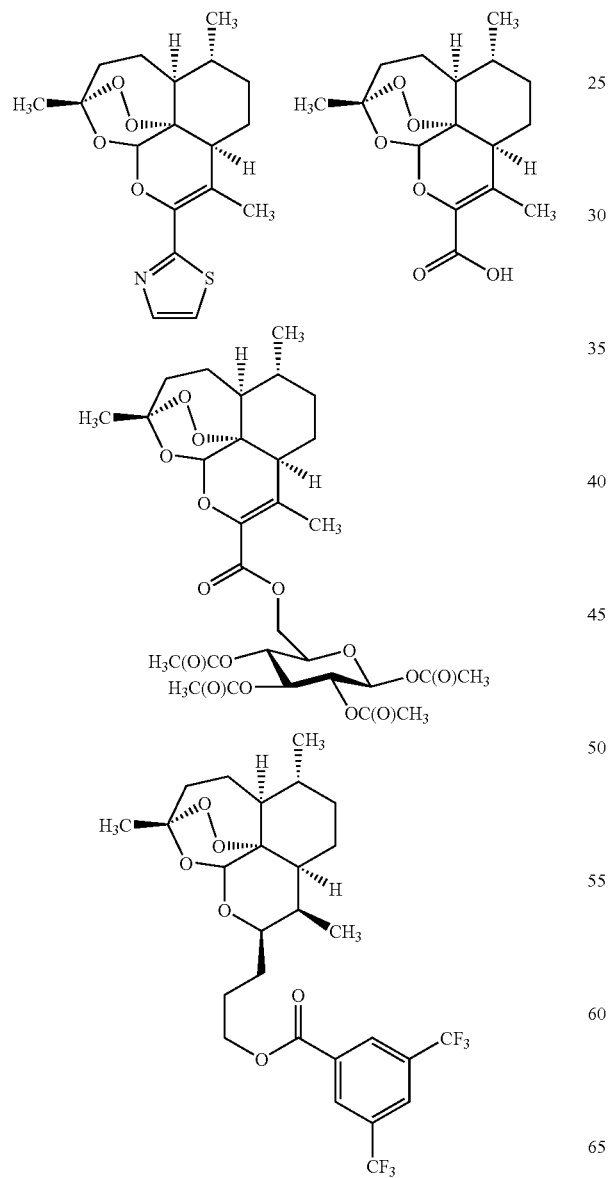

-continued

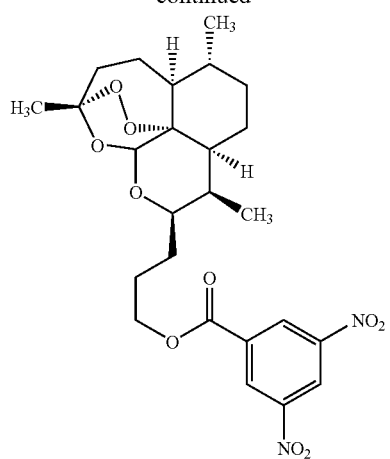

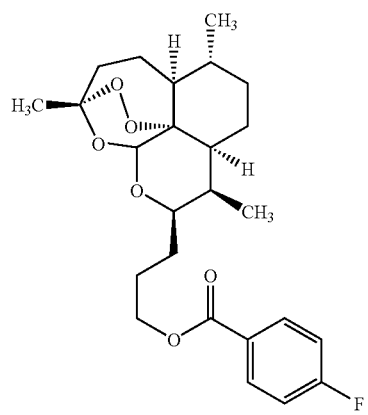

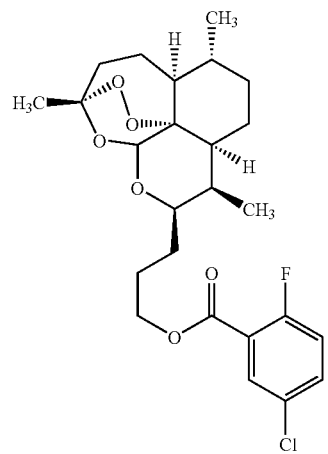

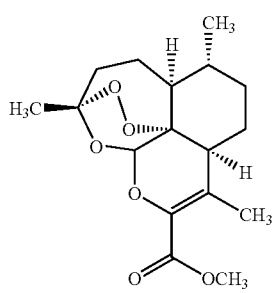

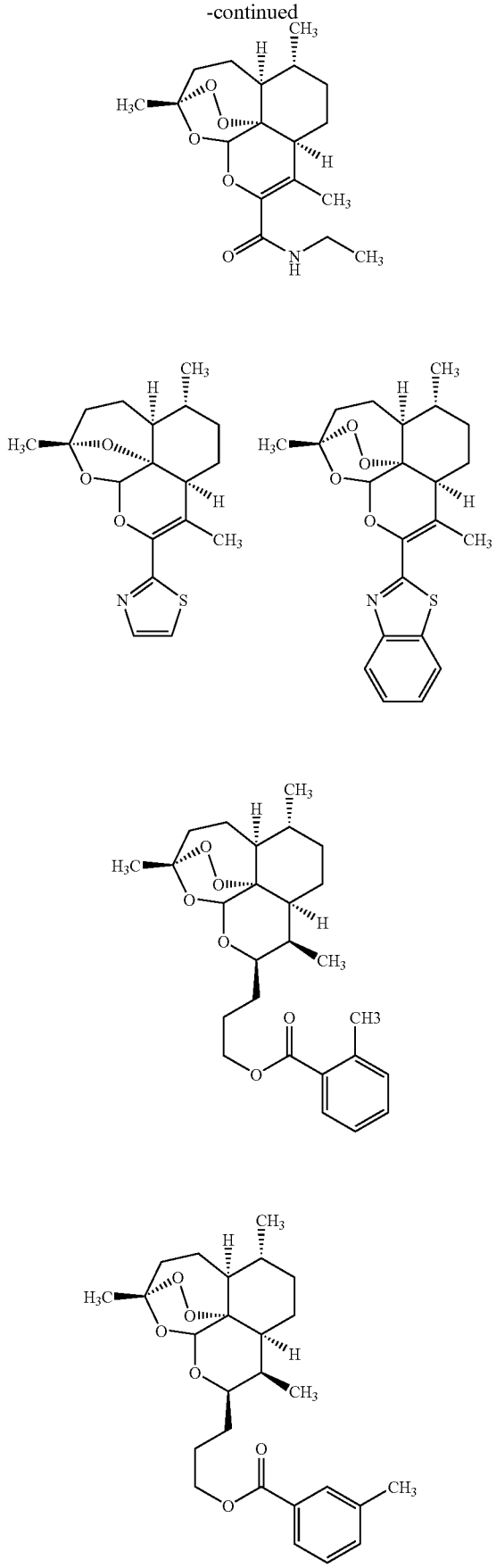

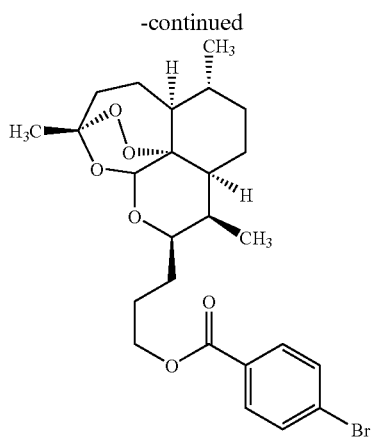
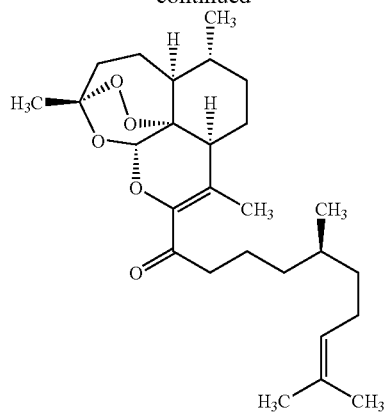
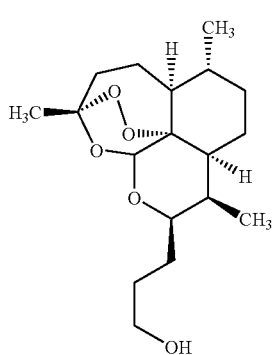
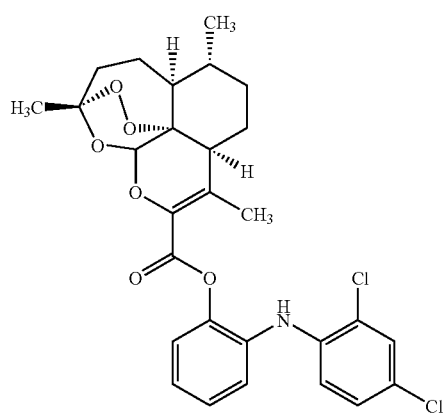
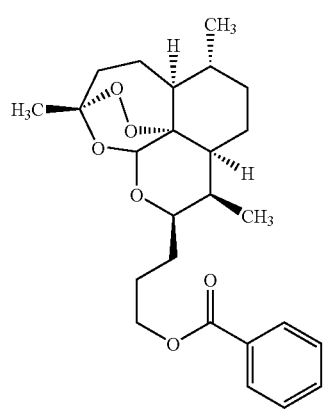
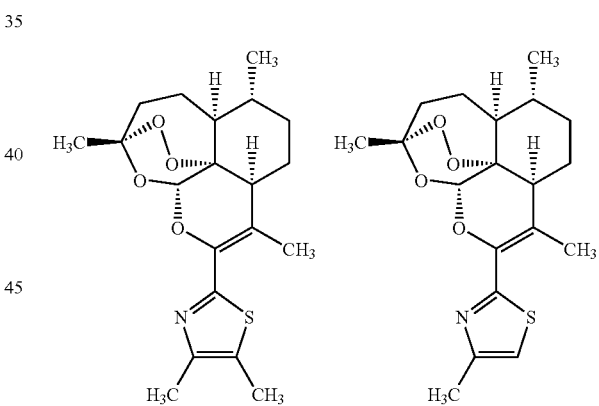
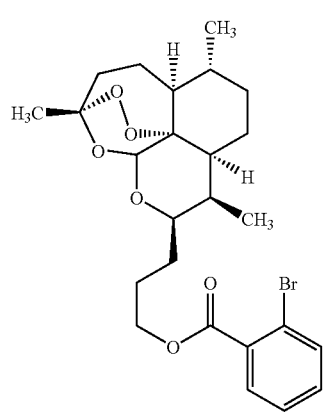
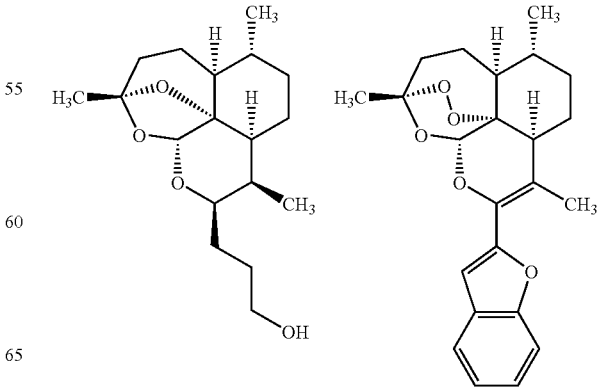

-continued

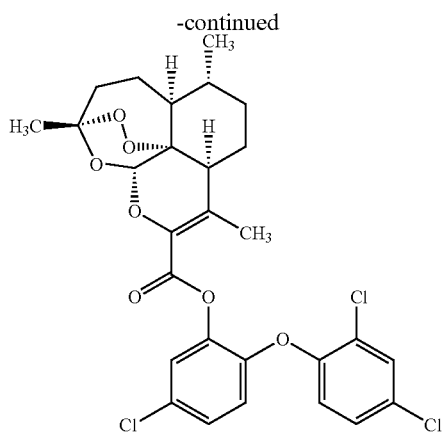

In another aspect, the disclosure provides pharmaceutical compositions having a compound of formula I in a pharmaceutically acceptable excipient.

In another aspect, the disclosure provides methods for preventing, controlling or treating an infectious disease in a subject in need of such treatment, comprising administering to the subject a therapeutically-effective amount of the pharmaceutical composition containing the compound of formula I.

In another aspect, the disclosure provides methods for preventing, controlling or treating an infectious disease in a subject in need of such treatment, comprising administering to the subject a therapeutically-effective amount of the pharmaceutical composition containing the compound of formula I, wherein the infectious disease is a parasitic disease selected from the group consisting of a *T. gondii* infection, trypanosome parasite infection, plasmodia parasite infection, and cryptosporidium parasite infection.

In another aspect, the disclosure provides methods for preventing, controlling or treating toxoplasma infection in a subject in need of such treatment, comprising administering to the subject a therapeutically-effective amount of the pharmaceutical composition containing the compound of formula I.

In another aspect, the disclosure provides methods for treating a psychiatric disorder associated with toxoplasma infection in a subject in need of such treatment, comprising administering to the subject a therapeutically-effective amount of the pharmaceutical composition containing the compound of formula I.

In another aspect, the disclosure provides methods for treating a psychiatric disorder associated with toxoplasma infection in a subject in need of such treatment, comprising administering to the subject a therapeutically-effective amount of the pharmaceutical composition containing the compound of formula I, wherein the psychiatric disorder is schizophrenia.

In another aspect, the disclosure provides methods for treating a psychiatric disorder associated with toxoplasma infection in a subject in need of such treatment, comprising administering to the subject a therapeutically-effective amount of a pharmaceutical composition, comprising a compound of formula I of claim 1, in combination with one or more antipsychotic drugs selected from chlorpromazine (Thorazine), haloperidol (Haldol), fluphenazine (Prolixin), thiothixene (Navane), trifluoperazine (Stelazine), perphenazine (Trilafon), and thioridazine (Mellaril), clozapine (Clozaril), risperidone (Risperdal), olanzapine (Zyprexa), quetiapine (Seroquel), ziprasidone (Geodon), and aripiprazole (Abilify), in a pharmaceutically acceptable excipient.

In another aspect, the disclosure provides methods for preparing a compound of formula I, the method comprising the steps of converting the compound of formula IV to the compound of formula I:

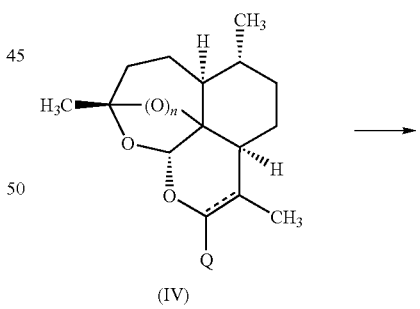

(IV)

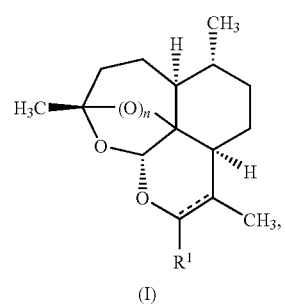

(I)

wherein:
- - - - - is a single or a double bond;
n is independently an integer from 1 to 2;
Q includes but is not limited to oxo, —(CH$_2$)$_t$OH or —C(O)OH, wherein each t is independently an integer from 1 to 6; and R$^1$ includes but is not limited to independently substituted or unsubstituted alkyl, substituted or unsubstituted aryl, substituted or unsubstituted arylalkyl, substituted or unsubstituted heteroaryl, substituted or unsubstituted heteroarylalkyl, —(CH$_2$)$_j$R$^2$, —(CH$_2$)$_j$O(CH$_2$)$_k$R$^2$, —(CH$_2$)$_j$C(O)(CH$_2$)$_k$R$^2$, —(CH$_2$)$_j$C(O)(CH$_2$)$_k$R$^2$, —(CH$_2$)$_j$C(O)O(CH$_2$)$_k$R$^2$, —(CH$_2$)$_j$NR$^3$R$^4$, —(CH$_2$)$_j$C(O)(CH$_2$)$_k$NR$^3$R$^4$, —(CH$_2$)$_j$NR$^5$C(O)(CH$_2$)$_k$R$^2$, —(CH$_2$)$_j$OC(O)(CH$_2$)$_k$NR$^3$R$^4$, —(CH$_2$)$_j$NR$^5$C(O)(CH$_2$)$_k$OR$^2$, —(CH$_2$)$_j$NR$^5$C(O)(CH$_2$)$_k$NR$^3$R$^4$, wherein each j and each k is independently an integer from 0 to 6; and m is independently an integer from 0 to 2;

R$^2$ includes but is not limited to hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, substituted or unsubstituted (aryl or heteroaryl)-X-(aryl or heteroaryl) wherein X is O, S, NH or N(C$_1$-C$_6$)alkyl, or a substituted or unsubstituted monosaccharide, and wherein each R$^2$ is optionally independently substituted with 1 to 5 R$^{10}$ groups;

R$^3$, R$^4$, and R$^5$ includes but are not limited to hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein R$^3$, R$^4$, and R$^5$, are each optionally independently substituted with 1 to 5 R$^{10}$ groups, or R$^3$ and R$^4$, together with the N atom to which they are attached, form substituted or unsubstituted heterocycloalkyl, or substituted or unsubstituted heteroaryl, wherein substituted or unsubstituted heterocycloalkyl, and substituted or unsubstituted heteroaryl are each optionally independently substituted with 1 to 5 R$^{10}$ groups, and R$^5$ is as described above; and each R$^{10}$ includes but is not limited to hydrogen, halogen, hydroxyl, amino, aminoalkyl, aminodialkyl, cyano, nitro, alkyl, —O-alkyl, —S-alkyl, perfluoroalkyl, —O-perfluoroalkyl, oxo, acetyl, or -benzyl.

In another aspect, the disclosure provides methods for preparing a compound of formula I, wherein - - - - - is a single bond; Q includes but is not limited to oxo; and R$^1$ includes but is not limited to substituted or unsubstituted aryl or substituted or unsubstituted heteroaryl.

In another aspect, the disclosure provides methods for preparing a compound of formula I, wherein Q includes but is not limited to —(CH$_2$)$_t$OH or —C(O)OH; and R$^1$ includes but is not limited to substituted or unsubstituted alkyl, —(CH$_2$)$_j$R$^2$, —(CH$_2$)$_j$O(CH$_2$)$_k$R$^2$, —(CH$_2$)$_j$C(O)(CH$_2$)$_k$R$^2$, —(CH$_2$)$_j$C(O)(CH$_2$)$_k$R$^2$, —(CH$_2$)$_j$C(O)O(CH$_2$)$_k$R$^2$, —(CH$_2$)$_j$NR$^3$R$^4$, —(CH$_2$)$_j$C(O)(CH$_2$)$_k$NR$^3$R$^4$, —(CH$_2$)$_j$NR$^5$C(O)(CH$_2$)$_k$R$^2$, —(CH$_2$)$_j$OC(O)(CH$_2$)$_k$NR$^3$R$^4$, —(CH$_2$)$_j$NR$^5$C(O)(CH$_2$)$_k$OR$^2$, or —(CH$_2$)$_j$NR$^5$C(O)(CH$_2$)$_k$NR$^3$R$^4$.

In another aspect, the disclosure provides compounds of formula I, prepared by any of the methods herein.

General Synthesis

The structures of artemisinin and artemisinin derivatives are shown in Scheme I.

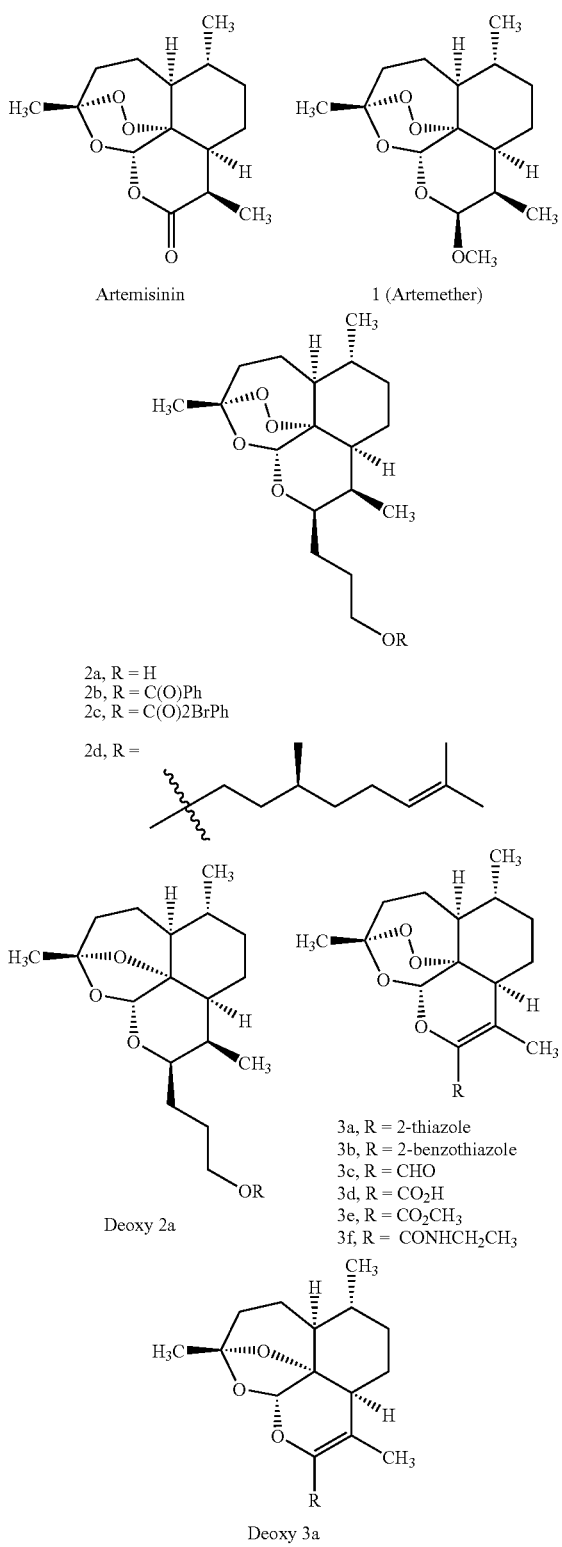

Scheme I

Artemisinin 1 (Artemether)

2a, R = H
2b, R = C(O)Ph
2c, R = C(O)2BrPh

2d, R =

Deoxy 2a

3a, R = 2-thiazole
3b, R = 2-benzothiazole
3c, R = CHO
3d, R = CO$_2$H
3e, R = CO$_2$CH$_3$
3f, R = CONHCH$_2$CH$_3$ Deoxy 3a The artemisinin derivatives described above may be prepared using procedures known to those of skill in the art. For example, trioxane C-10 primary alcohol 2a was prepared in 74% yield by hydroboration-oxidation of the corresponding known C-10 allyl trioxane. Esterification of primary alcohol 2a with benzoyl chloride led to benzoate ester 2b in 92% yield, whereas esterification with 2-bromo-benzoyl chloride produced 2-bromobenzoate ester 2c in 86% yield. Deprotonation of the primary alcohol 2a using sodium hydride and then displacement of the bromide anion from citronelyl bromide gave citronelyl ether 2d in 55% yield. Zinc-promoted deoxygenation of the known C-10 allyl trioxane and hydroboration-oxidation produced dioxolane deoxy-2a in 72% yield. Each of these new lipid-soluble chromatographically purified artemisinin derivatives was fully characterized spectroscopically (proton and carbon-13 nuclear magnetic resonance, infrared, and high-resolution mass spectrometry). In contrast to artemether, these trioxane monomers are hydrolytically stable for at least 12 h even at 60° C. in dimethyl sulfoxide-water at pH 7.4. Under these conditions, less than 5% decomposition was observed by proton nuclear magnetic resonance spectrometry.

Biological Activity

Normal human foreskin fibroblasts (American Type Culture Collection, Manassas, Va.) were used to grow tachyzoites and to test compounds for activity and cytotoxicity. Cells were maintained in Dulbecco's modified Eagle medium (Gibco, Grand Island, N.Y.) containing 10% fetal bovine serum (Atlas Biologicals, Fort Collins, Colo.), 25 mM HEPES (Gibco), 2 mM L-glutamine, 50 units of penicillin G per ml, and 50 µg of streptomycin sulfate per ml. A culture of the tachyzoites of $T.$ $gondii$ strain 2F, which constitutively expresses cytoplasmic β-galactosidase and is derived from strain RH (5), was a gift from Vern Carruthers, University of Michigan Medical School.

The compounds were tested for in vitro efficacy against $T.$ $gondii$ and cytotoxicity by previously published methods (9, 10). The median inhibitory dose (50% inhibitory dose [$ID_{50}$]) and the median cytotoxic dose (50% toxic dose [$TD_{50}$]) were calculated by extrapolation of the corresponding dose-response curve on a log-linear plot employing the portions of the curve that transected the 50% response point. For each compound, a therapeutic index (TI) was calculated by the formula $TI=TD_{50}/ID_{50}$.

FIG. 1 illustrates the quantification of invasion using red/green assay (8). Black bars represent internal/penetrated parasites while gray bars depict external/attached parasites. Compounds were tested at 10 µg/ml (range 25-34 µM). BAPTA-AM (20 µM) and cytochalasin D (Cyt D, 2 µM) were included as positive controls for inhibition of attachment or penetration, respectively. Data are mean values±SEM of three independent experiments, counting ten random fields for each sample. These data show that with the exception of artemisinin (ART) and derivative 3f, the compounds effectively inhibit the attachment of $T.$ $gondii$ tachyzoites to HFF cells. In addition, they moderately inhibit the penetration of the cells. Because the parasites are exposed to the compounds in vitro, i.e. in a test tube outside of the cells, these results suggest that some of the derivatives are active extracellularly as well as intracellularly (see Table 1). It is interesting to note that while deoxy-3a displays little or no efficacy in the growth inhibition assay (Table 1), it is effective in inhibition of attachment.

Figure 2:
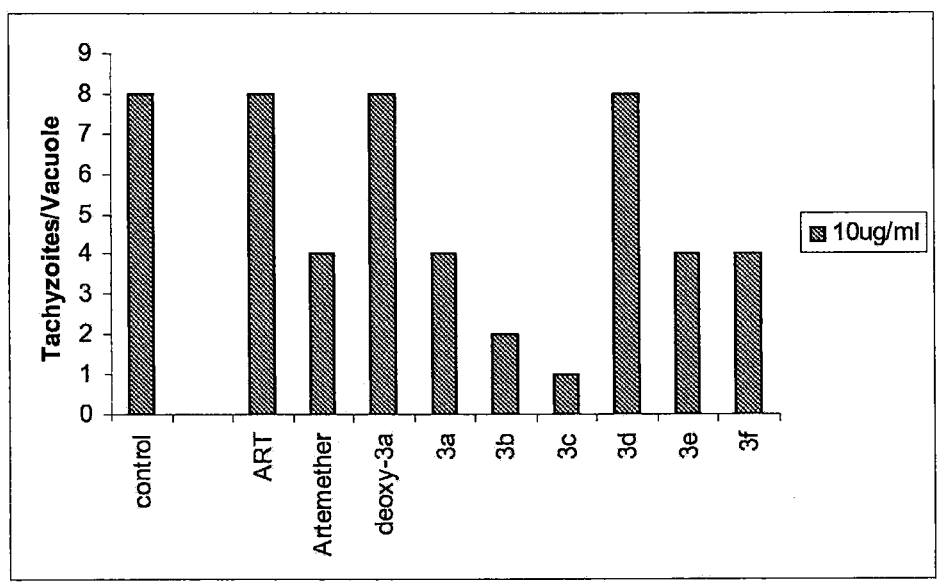
FIG. 2 illustrates the replication inhibition assay. *T. gondii* tachyzoites are allowed to infect HFF cells for 2 hours. Following this, compounds are added to the cells for a final concentration of 10 μg/ml and the infection is allowed to progress for 26 hours. Data are compiled from ten randomly selected fields wherein number of vacuoles and number of parasites within the vacuoles are enumerated. Control represents no drug added. These data show that derivatives 3c and 3b are quite effective as inhibitors of *T. gondii* replication whether they are added before the parasite, as in the data of Table 1, or after the parasite. Artemether, 3a, 3e and 3f show moderate inhibition while artemisinin, deoxy-3a and 3d are ineffective at this concentration.

FIG. 2 illustrates the replication inhibition assay (14). $T.$ $gondii$ tachyzoites are allowed to infect HFF cells for 2 hours. Following this, compounds are added to the cells for a final concentration of 10 µg/ml and the infection is allowed to progress for 26 hours. Data are compiled from ten randomly selected fields wherein number of vacuoles and number of parasites within the vacuoles are enumerated. Control represents no drug added. These data show that derivatives 3c and 3b are quite effective as inhibitors of $T.$ $gondii$ replication whether they are added before the parasite, as in the data of Table 1, or after the parasite. Artemether, 3a, 3e and 3f show moderate inhibition while artemisinin, deoxy-3a and 3d are ineffective at this concentration.

The results of the toxoplasma inhibition and cytotoxicity assays are shown in Tables 1 and 2.

TABLE 1

In vitro inhibition of $T.$ $gondii$ by artemisinin and synthetic derivatives

| Compound | Mol Wt | $ID_{50}$ | | $TD_{50}$ | | TI |
|---|---|---|---|---|---|---|
| | | µg/ml | µM | µg/ml | µM | |
| Artemisinin | 282.34 | 2.3 | 8.0 | >320[b] | >1,130 | ≧243 |
| Artemether | 298.4 | 0.2 | 0.7 | 220 | 740 | 1,100 |
| 2d | 464.68 | 0.5 | 1.1 | 160 | 340 | 320 |
| 2c | 509.43 | 0.6 | 1.2 | >320[b] | >630 | ≧933 |
| 2b | 430.54 | 0.6 | 1.4 | >320[b] | >740 | ≧933 |
| 2a | 326.43 | 2.7 | 8.3 | 510 | 1,560 | 190 |
| Deoxy-2a | 310.43 | 173 | 560 | 200 | 640 | 1.2 |
| Trimethoprim | 290.3 | 5.2 | 17.9 | 60 | 210 | 12 |

TABLE 2

In vitro inhibition of $T.$ $gondii$ by novel derivatives of artemisinin

| Compound | Code | $ID_{50}$[a] | | $TD_{50}$[a] | | TI[b] |
|---|---|---|---|---|---|---|
| | | µg/ml (SEM[c]) | µM | µg/ml | µM | |
| DART-ald | 3c | 0.3 (0.02) | 1.0 | 26 | 89 | 92 |
| DART-benzothiaz | 3b | 0.4 (0.12) | 1.0 | 9 | 23 | 28 |
| DART-thiaz | 3a | 0.6 (0.09) | 1.7 | ≧320 | 916 | 975 |
| DART-C(O)-Ome | 3e | 0.9 (0.15) | 2.9 | 177 | 545 | 210 |
| DART-C(O)-NHEt | 3f | 1.5 (0.32) | 4.4 | 72 | 215 | 52 |
| DART-COOH | 3d | 12.5 (3.6) | 40.3 | ≧320 | 1031 | 60 |
| Deoxy-DART-thiaz | Deoxy-3a | 320 | 959.7 | ≧320 | 960 | 1.8 |
| Artemether | | 0.11 | 0.37 | 200 | 669 | 1818 |
| Trimethoprim | | 5.5 | 19 | 60 | 207 | 11 |

[a]The average $ID_{50}$ and $TD_{50}$ from three independent experiments are shown. Derivatives are listed in decreasing order of efficacy according to $ID_{50}$.
[b]TI = $TD_{50}/ID_{50}$
[c]SEM = Standard error of the mean derived from the $ID_{50}$ from three experiments.

Artemether, 2b, 2c, and 2d all inhibited the toxoplasma at concentrations of less than 1 µg/ml (Table 1). Somewhat less antitoxoplasma activity was noted with artemisinin and compound 2a, which inhibited toxoplasma replication at concentrations between 2 and 3 µg/ml. These values compare favorably to that of the antifolate positive-control compound trimethoprim, which inhibited toxoplasma replication at a concentration of 5.2 µg/ml. Nonperoxidic deoxy-2a showed virtually no inhibitory activity against the toxoplasma, with a TI of 1.2.

It was found six 9,10-dehydro-artemisinin (DART) derivatives, as well as one non-peroxidic deoxy-DART version, potently inhibit one or more of the following: growth, replication, invasion and/or attachment of $Toxoplasma$ $gondii$ parasites in and to cells (Table 2, FIGS. 1 and 2).

In order to determine therapeutic indices and thus specific antitoxoplasma activity, we also measured the cytotoxicity of the test compounds. Artemisinin, 2a, 2b, 2c, 3a, and 3d showed little cytotoxicity at concentrations up to 510 μg/ml (compound 2a) or 320 μg/ml while artemether, 2d, and 3e showed 50% cytotoxicity only at concentrations of >160 μg/ml (Tables 1 and 2). These degrees of cytotoxicity compare favorably with that of trimethoprim, with a TD50 of 60 μg/ml. The therapeutic indices of all of the compounds except deoxy-2a and deoxy-3a were approximately 3× to 100× more favorable than that of trimethoprim.

All of the compounds that showed inhibitory activity in our assays towards *T. gondii* have been shown to inhibit the replication of chloroquine-sensitive *Plasmodium falciparum* (NF 54) strains of malaria with $ID_{50}s$ from 5 to 30 nM (J. D'Angelo and G. Posner, unpublished data). And further, as expected (3), nonperoxidic deoxy-2a and deoxy-3a, which have virtually no antimalaria activity (J. D'Angelo and G. Posner, unpublished data), was also devoid of antitoxoplasma activity. These findings suggest that derivatives of artemisinin may affect similar pathways in toxoplasma and malarial organisms. The elucidation of these shared pathways should be the subject of additional investigations.

We have demonstrated that the new nonacetal derivatives of artemisinin have both increased antitoxoplasma activity and decreased cytotoxicity compared to trimethoprim, one of the antifolate compounds of relatively low toxicity that is used for the treatment of toxoplasma infection in humans. While other antifolate compounds, such as pyrimethamine, have increased antitoxoplasma activity, their toxicity generally precludes wide-spread usage, particularly over prolonged periods of administration (6). The availability of low-toxicity compounds capable of the prevention and treatment of *T. gondii* in humans represents a major advance in the treatment of infections in immunocompromised individuals. Further, the availability of such compounds would also allow for clinical trials directed at defining the role of toxoplasma infections in human diseases.

Methods of Treatment

The evidence linking infection with *T. gondii* to the etiology of schizophrenia is well known (16). Epidemiologic studies have indicated that infectious agents may contribute to some cases of schizophrenia. In animals, infection with *T. gondii* can alter behavior and neurotransmitter function. In humans, acute infection with *T. gondii* can produce psychotic symptoms similar to those displayed by persons with schizophrenia. Since 1953, a total of 19 studies of *T. gondii* antibodies in persons with schizophrenia and other severe psychiatric disorders and in controls have been reported; 18 reported a higher percentage of antibodies in the affected persons; in 11 studies the difference was statistically significant. Two other studies found that exposure to cats in childhood was a risk factor for the development of schizophrenia. Some medications used to treat schizophrenia inhibit the replication of *T. gondii* in cell culture (10). Establishing the role of *T. gondii* in the etiopathogenesis of schizophrenia may lead to new medications for its prevention and treatment.

Schizophrenia is a pervasive neuropsychiatric disease of uncertain cause that affects approximately 1% of the adult population in the United States and Europe. An increased occurrence of schizophrenia in family members of affected persons suggests that genetic factors play a role in its etiology, and some candidate predisposing genes have been identified. Environmental factors are also important. Epidemiologic studies, for example, have established that winter-spring birth, urban birth, and perinatal and postnatal infection are all risk factors for the disease developing in later life. These studies have rekindled an interest in the role of infectious agents in schizophrenia, a concept first proposed in 1896.

*T. gondii* is an intracellular parasite in the phylum Apicomplexa. Its life cycle can be completed only in cats and other felids, which are the definitive hosts. However, *T. gondii* also infects a wide variety of intermediate hosts, including humans. In many mammals, *T. gondii* is known to be an important cause of abortions and stillbirths and to selectively infect muscle and brain tissue. A variety of neurologic symptoms, including incoordination, tremors, head-shaking, and seizures, have been described in sheep, pigs, cattle, rabbits, and monkeys infected with *T. gondii*. Humans may become infected by contact with cat feces or by eating undercooked meat. The importance of these modes of transmission may vary in different populations. Individual response to *Toxoplasma* infection is determined by immune status, timing of infection, and the genetic composition of the host and the organism.

*Toxoplasma* organisms have also been shown to impair learning and memory in mice and to produce behavioral changes in both mice and rats. Of special interest are studies showing that *Toxoplasma*-infected rats become less neophobic, leading to the diminution of their natural aversion to the odor of cats. These behavioral changes increase the chances that the rat will be eaten by a cat, thus enabling *Toxoplasma* to complete its life cycle, an example of evolutionarily driven manipulation of host behavior by the parasite.

In humans, *Toxoplasma* is an important cause of abortions and stillbirths after primary infection in pregnant women. The organism can also cross the placenta and infect the fetus. The symptoms of congenital toxoplasmosis include abnormal changes in head size (hydrocephaly or microcephaly), intracranial calcifications, deafness, seizures, cerebral palsy, damage to the retina, and mental retardation. Some sequelae of congenital toxoplasmosis are not apparent at birth and may not become apparent until the second or third decade of life. Hydrocephalus, increased ventricular size, and cognitive impairment have also been noted in some persons with schizophrenia and other forms of psychosis.

Some cases of acute toxoplasmosis in adults are associated with psychiatric symptoms such as delusions and hallucinations. Schizophrenia was first diagnosed in these patients, but later neurologic symptoms developed, which led to the correct diagnosis of *Toxoplasma* encephalitis.

Chlorpromazine (Thorazine) is the first antipsychotic medication used for schizophrenia. This was soon followed by other medications such as haloperidol (Haldol), fluphenazine (Prolixin), thiothixene (Navane), trifluoperazine (Stelazine), perphenazine (Trilafon), and thioridazine (Mellaril). These medications have become known as "neuroleptics" because, although effective in treating positive symptoms (ie, acute symptoms such as hallucinations, delusions, thought disorder, loose associations, ambivalence, or emotional lability), cause side effects, many of which affect the neurologic (nervous) system.

A new class of antipsychotics (atypical antipsychotics) was introduced after 1989. At clinically effective doses, no (or very few) of these neurological side effects, which often affect the extrapyramidal nerve tracts (which control such things as muscular rigidity, painful spasms, restlessness, or tremors) are observed. The first of the new class, clozapine (Clozaril) is the only agent that has been shown to be effective where other antipsychotics have failed. Its use is not associated with extrapyramidal side effects, but it does produce other side effects, including possible decrease in the number of white cells, so the blood needs to be monitored every week during the first 6 months of treatment and then every 2 weeks to catch this side effect early if it occurs. Other atypical antipsychotics include risperidone (Risperdal), olanzapine (Zyprexa), quetiapine (Seroquel), ziprasidone (Geodon), and aripiprazole (Abilify). The use of these medications has allowed successful treatment and release back to their homes and the community for many people suffering from schizophrenia.

Thus, in another aspect the disclosure provides combinations of the compound of formula I, and an antipsychotic drug, including but not limited to chlorpromazine (Thorazine), haloperidol (Haldol), fluphenazine (Prolixin), thiothixene (Navane), trifluoperazine (Stelazine), perphenazine (Trilafon), and thioridazine (Mellaril), clozapine (Clozaril), risperidone (Risperdal), olanzapine (Zyprexa), quetiapine (Seroquel), ziprasidone (Geodon), and aripiprazole (Abilify), for the treatment of schizophrenia.

Protecting Groups

The compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking or protecting groups include, for example:

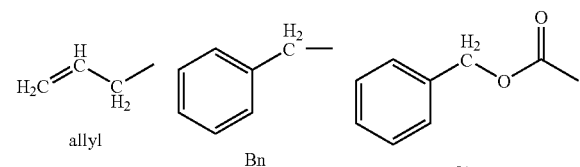

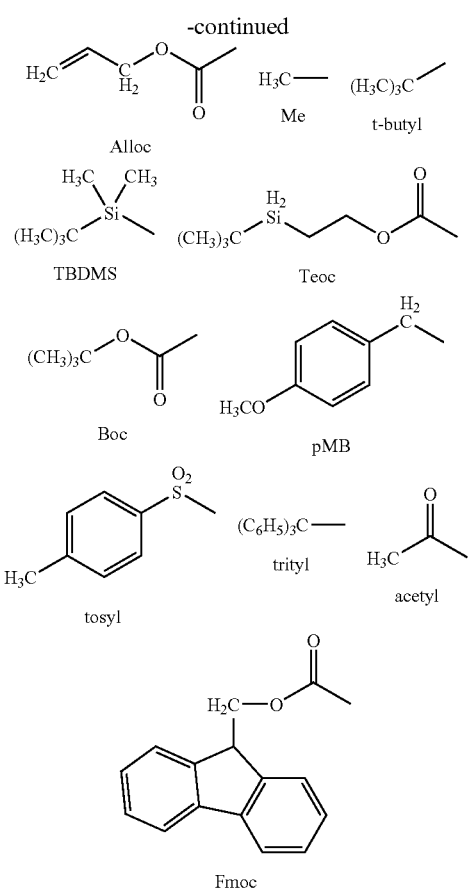

Pharmaceutical Compositions and Administration

In another aspect, the present disclosure relates to a pharmaceutical composition including a triazalopyridazine kinase modulator in admixture with a pharmaceutically acceptable excipient. One of skill in the art will recognize that the pharmaceutical compositions include the pharmaceutically acceptable salts of the triazalopyridazine kinase modulators described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other anti-proliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this disclosure may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present disclosure is not to be limited in scope by the exemplified embodiments, which are intended as illustrations of single aspects of the disclosure. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the disclosure. References cited throughout this application are examples of the level of skill in the art and are hereby incorporated by reference herein in their entirety for all purposes, whether previously specifically incorporated or not.

EXAMPLES

The following examples are offered to illustrate, but not to limit the claimed disclosure.

Artemisinin was obtained from Holley Pharmaceuticals Co., Inc., Fullerton, Calif. Artemether was generously donated by Huiling Wang, University of Wuhan, China. Trimethoprim was purchased from Sigma Chemical Co. (St. Louis, Mo.). Chlorophenol red-β-D-galactopyranoside (Roche, Indianapolis, Ind.), 100 mM in 100 mM HEPES (pH 7.2), was stored frozen at −80° C. CellTiter 96 AQ$_{ueous}$ One Solution Reagent for determining cytotoxicity was purchased from Promega Corp., Madison, Wis.

As used herein, the term "ART" refers to fragment:

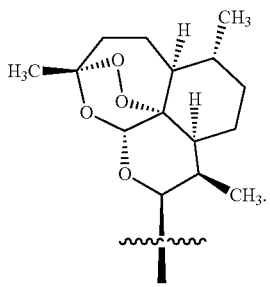

For example, the phrase "ART-PrOH" refers to structure:

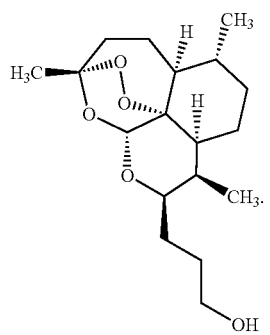

As used herein, the term "DART" refers to fragment

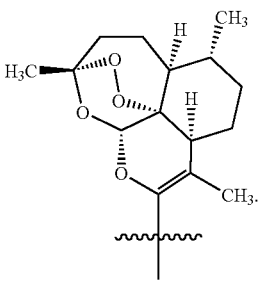

For example, the phrase "DART-PrOH" refers to structure:

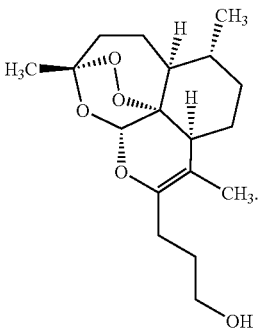

As used herein, "Deoxy-ART" refers to fragment

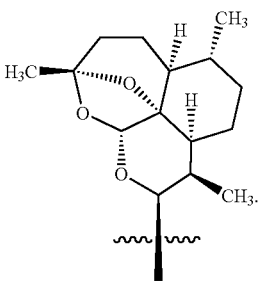

For example, the phrase "Deoxy-ART-PrOH" refers to structure:

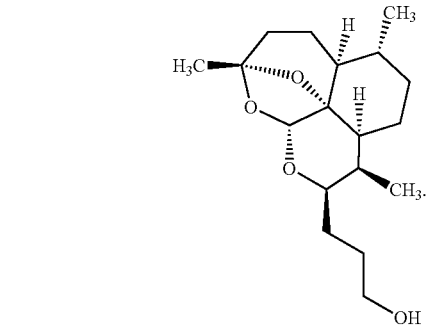

As used herein, "Deoxy-DART" refers to fragment

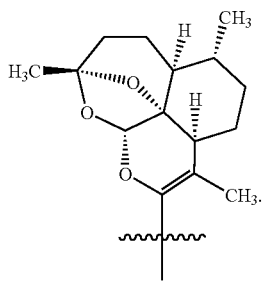

For example, the phrase "Deoxy-DART-PrOH" refers to structure:

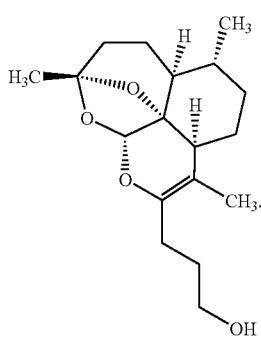

Example 1

DART-Thiaz

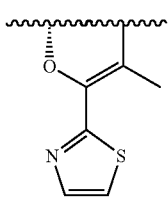

A flame-dried 100 mL round-bottomed flask, RBF, was loaded with a stir-bar, diethyl ether (Et₂O), and 2-bromothioazole (0.88 mL, 9.92 mmol). The flask was immersed into a dry ice/acetone bath and after several minutes, n-BuLi (6.2 mL, 1.6 M sol in hexanes, 9.92 mmol) was added over 14 minutes. The mixture was stirred for 42 minutes at which time artemisinin (2 g, 7.08 mmol) in tetrahydrofuran (THF) (40 mL) was added over 18 minutes. After 45 minutes, acetic anhydride (4.8 mL, 50.3 mmol) was added and the dry ice/acetone bath was replaced with an ice water bath. The mixture rapidly became thick and a larger stir bar was added. After 2.5 hr, BF₃ etherate (9 mL, 70 mmol) was added and the mixture became thinner and stirred freely. It was then stirred overnight, poured into a separatory funnel containing dichloromethane (DCM) (200 mL) and saturated aqueous sodium bicarbonate (100 mL). The organic layer was washed 2 additional times with saturated aqueous sodium bicarbonate, once with saturated aqueous sodium chloride, dried with magnesium sulfate, filtered and evaporated. The residue was purified twice by flash column chromatography (first column: gradient, silica gel, packed with 100% hexanes, eluted with 10% ethyl acetate in hexanes, then 17% ethyl acetate in hexanes; second column: silica gel, packed with 100% hexanes, eluted with 10% ethyl acetate in hexanes) to give the product as an off-white amorphous solid (1.42 g, 4.06 mmol, 57%). ¹H NMR (CDCl₃, 400 MHz): δ 7.84-7.83 (d, J=4 Hz, 1H), 7.31-7.3 (d, J=4 Hz, 1H), 5.79 (s, 1H), 2.49-2.38 (m, 1H), 2.27 (s, 3H), 2.15-2.04 (m, 2H), 2.01-1.92 (m, 2H), 1.78-1.07 (m, 9H), 1.02-1.00 (d, J=8 Hz, 3H). ¹³C NMR (CDCl₃, 100 MHz): δ 165.1, 142.8, 138.1, 118.4, 110.8, 104.6, 90.3, 78.5, 50.7, 48.0, 37.6, 35.1, 34.2, 29.1, 25.7, 24.5, 20.2, 17.2.

Example 2

DART-4-Me-thiaz

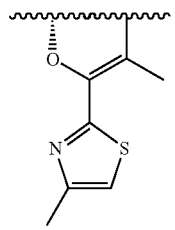

A flame-dried 2 dram vial was loaded with a stir-bar, diethyl ether (880 μL), and 4-methylthiazole (17 μL, 0.18 mmol). The vial was immersed in a dry ice/acetone bath and after several minutes, n-BuLi (110 μL, 1.6 M sol in hexanes, 0.18 mmol) was added over a one minute period. The mixture was stirred for 45 minutes at which time the thiazole solution was added to a cooled (−78° C.) solution of artemisinin (50 mg, 0.18 mmol) in THF (880 μL) over 5 minutes. After 60 minutes, acetic anhydride (125 μL, 1.3 mmol) was added and the dry ice/acetone bath was replaced with an ice water bath. After two hours, BF₃ etherate (160 μL, 1.3 mmol) was added and the cooling bath was removed. The reaction was allowed to warm to room temperature, RT, and stir at RT for two hours at which time the colorless mixture had turned light yellow. The reaction mixture was then poured into a separatory funnel containing dichloromethane (10 mL) and saturated aqueous sodium bicarbonate (5 mL). The organic layer was washed two additional times with saturated aqueous sodium bicarbonate (5 mL), once with saturated aqueous sodium chloride (5 mL), dried with magnesium sulfate, filtered, and concentrated, in vacuo, at 40° C. to afford 73 mg of crude product. The residue was purified by flash column chromatography (8.6 grams of silica gel; packed with 100% hexanes; eluted with 10% ethyl acetate in hexanes) to give the product as a white crystalline solid (24 mg, 0.07 mmol, 36.7%). ¹H NMR (CDCl₃, 400 MHz): δ 6.82 (s, 1H), 5.75 (s, 1H), 2.45-2.37 (m, 4H), 2.23 (s, 3H), 2.11-2.02 (m, 2H), 1.98-1.88 (m, 2H), 1.73-1.69 (m, 1H), 1.61-1.55 (m, 1H), 1.46-1.44 (m, 4H), 1.36-1.24 (m, 2H), 1.19-1.09 (m, 1H), 1.00-0.99 (d, J=1.2 Hz, 3H). ¹³C NMR (CDCl₃, 100 MHz): δ 164.1, 152.7, 138.2, 113.1, 110.3, 104.5, 90.3, 78.4, 50.7, 47.9, 37.6, 36.1, 34.2, 29.0, 25.6, 24.5, 20.1, 17.4, 17.1.

Example 3

DART-4,5-DiMe-thiaz

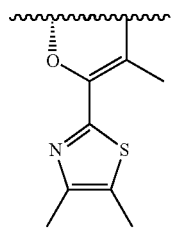

A flame-dried 2 dram vial was loaded with a stir-bar, diethyl ether (880 μL), and 2-iodo-4,5-dimethylthiazole (42 mg, 0.18 mmol). The vial was immersed in a dry ice/acetone bath and after several minutes, n-BuLi (110 μL, 1.6 M sol in hexanes, 0.18 mmol) was added over a one minute period. The mixture was stirred for 45 minutes at which time the thiazole solution was added to a cooled (−78° C.) solution of artemisinin (50 mg, 0.18 mmol) in THF (880 μL) over 5 minutes. After 60 minutes, acetic anhydride (125 μL, 1.3 mmol) was added and the dry ice/acetone bath was replaced with an ice water bath. After two hours, $BF_3$ etherate (160 μL, 1.3 mmol) was added and the cooling bath was removed. The reaction was allowed to warm to RT and stir at RT for two hours at which time the colorless mixture had turned light yellow. The reaction mixture was then poured into a reparatory funnel containing dichloromethane (10 mL) and saturated aqueous sodium bicarbonate (5 mL). The organic layer was washed two additional times with saturated aqueous sodium bicarbonate (5 mL), once with saturated aqueous sodium chloride (5 mL), dried with magnesium sulfate, filtered, and concentrated, in vacuo, at 40° C. to afford 82 mg of crude product. The residue was purified by flash column chromatography (12.2 grams of silica gel; packed with 100% hexanes; eluted with 5% ethyl acetate in hexanes) to give the product as a foam (22 mg, 0.07 mmol, 32.9%). $^1$H NMR ($CDCl_3$, 400 MHz): δ 5.72 (s, 1H), 2.44-2.36 (m, 1H), 2.34 (s, 3H), 2.32 (s, 3H), 2.18 (s, 3H), 2.08-2.02 (m, 2H), 1.95-1.85 (m, 2H), 1.72-1.68 (m, 1H), 1.61-1.51 (m, 1H), 1.46-1.43 (m, 4H), 1.38-1.25 (m, 2H), 1.19-1.08 (m, 1H), 0.99-0.98 (d, J=1.2 Hz, 3H). $^{13}$C NMR ($CDCl_3$, 100 MHz): δ 159.8, 148.2, 138.2, 125.8, 109.3, 104.5, 90.2, 78.4, 50.7, 47.9, 37.6, 36.1, 34.2, 29.0, 25.6, 24.5, 20.1, 17.1, 14.9, 11.2.

Example 4

DART-Benzothiazole

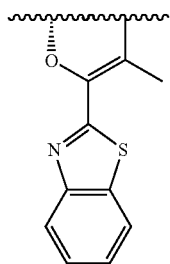

A 10 mL flame-dried RBF was loaded with a stir-bar and diethyl ether (2 mL). Benzothiazole (0.26 mL, 2.39 mmol) was added and the system was immersed in a dry ice-acetone bath. After cooling, n-BuLi (1.0 mL, 1.6 mmol) was added over 13 minutes, the solution becoming slightly yellow. Over about 30 minutes, the solution became more orange and slightly cloudy. A solution of artemisinin (150 mg, 0.53 mmol) in THF (2 mL) was then transferred from a flame-dried 5 mL RBF via cannula. After 45 minutes, the TLC showed all the artemisinin was consumed. The solution was allowed to stir an additional 15 minutes and acetic anhydride (0.5 mL, 5.3 mmol) was added in one portion. The solution became very thick and THF (2 mL) was added. The reaction was stirred overnight during which time the ice bath expired. After stirring overnight, $BF_3$ etherate (1.66 mL, 13.25 mmol) was added and after several minutes, triethylamine, TEA, (2 mL) was added to quench the reaction. The mixture was then poured into a separatory funnel containing dichloromethane and saturated aqueous sodium bicarbonate. The aqueous layer was extracted with dichloromethane (3×50 mL) and the combined organics were washed with saturated aqueous sodium chloride, dried with magnesium sulfate, filtered, and evaporated. The residue was purified by flash column chromatography (silica gel, 100% hexanes then 7% ethyl acetate in hexanes) to give DART-benzothiazole (114.2 mg, 0.29 mmol, 54%). $^1$H NMR ($CDCl_3$, 400 MHz): δ 8.04-8.02 (d, J=8 Hz, 1H), 7.91-7.9 (d, J=8 Hz, 1H), 7.49-7.44 (m, 1H), 7.39-7.35 (m, 1H), 2.49-2.41 (m, 1H), 2.37 (s, 3H), 2.16-2.1 (m, 2H), 2.08-2.06 (m, 2H), 1.78-1.74 (m, 1H), 1.64-1.2 (m, 9H), 1.04-1.02 (d, J=6 Hz, 3H), 0.99-0.88 (m, 1H). $^{13}$C NMR ($CDCl_3$, 100 MHz): δ 165.0, 153.8, 138.3, 134.7, 125.7, 124.7, 123.1, 121.3, 113.7, 104.7, 90.5, 78.3, 50.6, 48.3, 37.6, 36.1, 34.2, 29, 25.7, 24.5, 20.1, 17.5. IR (thin film): 2871, 1651, 1457, 1442, 1109, 948, 732. HRMS FAB$^+$ calculated for $C_{22}H_{26}NO_4S^+$: 400.15826, found 400.15724. $[α]_D^{26}$=+31.08 (c 2.55, $CHCl_3$).

Example 5

DART-Benzofuran

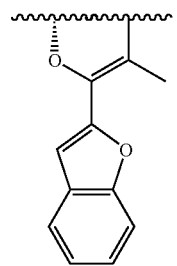

A 10 mL flame-dried RBF was loaded with a stir-bar, 2-bromo-1-benzofuran (160.3 mg, 0.81 mmol), and ether (3 mL). An addition 10 mL flame-dried RBF was loaded with a stir bar, artemisinin (67.4 mg, 0.24 mmol) and THF (3 mL). Both flasks were immersed into dry ice/acetone baths and n-BuLi (0.33 mL, 1.6 M sol, 0.53 mmol) was added over 14 minutes to the flask containing the 2-bromo-1-benzofuran which was then stirred at RT for nine minutes. The flask was then re-immersed in the dry ice/acetone bath. The resulting solution became pale yellow. After 41 additional minutes, the artemisinin solution was added via cannula and the resulting solution became deeper orange in color. After 30 minutes of stirring at −78° C., the TLC showed consumption of artemisinin and the formation of 2 new spots, with a lower $R_f$. Acetic anhydride (0.14 mL, 1.51 mmol) was added 25 minutes later. After for 2 hours, the new spot was observed to have disappeared, triethylsilane (0.68 mL, 4.21 mmol), and trimethylsilyl trifluorosulfonate (0.58 mL, 3.2 mmol) were added and the reaction became fuchsia in color. Then, TEA (2 mL) was added 2.5 hours later. The reaction was then poured into a reparatory funnel containing dichloromethane and saturated aqueous sodium bicarbonate. The organic layer was washed with saturated aqueous sodium bicarbonate (3×30 mL). The organic layer was then washed with saturated aqueous sodium chloride, dried over magnesium sulfate, filtered, and evaporated. The residue was purified using two flash chromatography columns (first column: silica gel, packed with 100% hexanes, eluted with 5% ethyl acetate in hexanes; second column: silica gel, packed with 100% hexanes, eluted with 50% dichloromethane in hexanes) to give the product as a

Example 6

DART-2-Pyridine

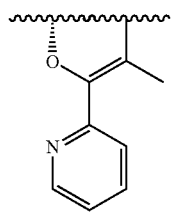

A 10 mL flame-dried RBF was loaded with a stir-bar, 2-bromopyridine (0.05 mL, 0.53 mmol), and diethyl ether (3 mL). An second 10 mL flame-dried RBF was loaded with a stir-bar, artemisinin (64.2 mg, 0.23 mmol), and THF (3 mL). Both flasks were immersed into dry ice/acetone baths and n-BuLi (0.33 mL, 1.6 M sol, 0.53 mmol) was added over 21 minutes to the flask containing the 2-bromopyridine. The resulting solution became orange-red. After 24 additional minutes, the solution of artemisinin was added via cannula and the resulting solution turned darker in color. After 30 minutes of stirring at −78° C., the TLC showed consumption of artemisinin and the formation of a new spot. Acetic anhydride (0.14 mL, 1.51 mmol) was added 15 minutes later. After stirring overnight, the new spot was observed to have disappeared and $BF_3$ etherate (0.53 mL, 4.26 mmol) was added, followed by TEA (2 mL), 10 minutes later. The reaction was then poured into a reparatory funnel containing dichloromethane and ~10% aqueous hydrochloric acid. The aqueous layer was extracted with dichloromethane (3×30 mL). The combined organics were then washed with saturated aqueous sodium chloride, dried over magnesium sulfate, filtered, and evaporated. The residue was purified with two flash chromatography columns (first column: silica gel, packed with 100% hexanes, eluted with 25% ethyl acetate in hexanes; second column: silica gel, packed with 100% hexanes, eluted with 20% ethyl acetate in hexanes) to give the product as a powdery white solid (35.3 mg, 0.10 mmol, 44.7%). $^1$H NMR (CDCl$_3$, 300 MHz): δ 8.57-8.56 (m, 1H), 7.70-7.59 (m, 2H), 7.17-7.12 (m 1H), 5.75 (s, 1H), 2.47-2.37 (m, 1H), 2.14-1.81 (m, 7H), 1.73-1.31 (m, 8H), 1.24-1.06 (m, 1H), 1.03-0.995 (d, J=11 Hz, 3H). $^{13}$C NMR (CDl$_3$, 100 MHz): δ 155.1, 148.2, 143, 136.1, 123.6, 122.1, 123.6, 122.1, 108.1, 104.5, 90.4, 78.7, 50.9, 47.4, 37.7, 36.3, 34.3, 29.2, 25.9, 24.5, 20.2, 16.9. IR (thin film): 2406, 1675, 1658, 1122, 1113. HRMS (FAB$^+$) calculated for $C_{20}H_{26}NO_4^+$: 344.1862, found 344.1858. $[\alpha]_D^{26}$=+133.26 (c 1.45, CHCl$_3$).

Example 7

DART-C(O)—O-tetraAcglucapyranose

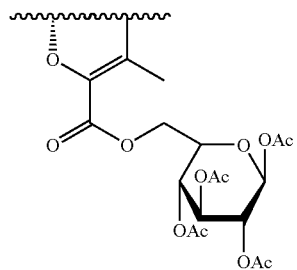

A 25 mL flame-dried round RBF was loaded with DART-COOH (37.1 mg, 0.12 mmol), catalytic 4-(N,N-dimethylamino)pyridine, DMAP, (5.8 mg), dicyclohexyl carbodiimide, DCC, (65.2 mg, 0.32 mmol), 1,2,3,4-tetra-O-acetyl β-D-glucopyranose (100.2 mg, 0.29 mmol), and a stir-bar. Dichloromethane (10 mL) was then added, and the mixture was stirred overnight at RT. Then additional DMAP (15 mg) was added and the mixture was allowed to stir at RT for an additional 24 hours. After evaporation of most of the solvent, the residue was purified by flash column chromatography (silica gel, 20% pet ether in diethyl ether) to give DART-C(O)—OtetraAcglucapyranose (43.8 mg, 0.07 mmol, 57%) as an amorphous white solid. $^1$H NMR (400 MHz, CDCl$_3$): δ 5.73-5.71 (d, J=7 Hz, 1H), 5.63 (s, 1H), 5.29-5.24 (t, 9 Hz, 1H), 5.16-5.07 (m, 2H), 4.34-4.26 (m, 2H), 3.99-3.93 (m, 1H), 2.43-2.35 (m, 1H), 2.1 (s, 3H), 2.04-1.98 (m, 14H), 1.94-1.84 (m, 3H), 1.7-1.04 (m, 14H), 0.98-0.95 (d, J=12 Hz, 3H). $^{13}$C NMR (100 MHz, CDCl$_3$): δ 170.1, 169.3, 169.2, 168.8, 162.6, 135.7, 121.1, 104.6, 91.6, 90.0, 78, 72.8, 72.6, 70.3, 68.7, 62.7, 50.6, 49.1, 48.3, 37.5, 36.1, 34.1, 34, 28.8, 25.6, 25.60, 24.9, 24.3, 20.7, 20.6, 20.1, 17.8. IR (thin film): 2930, 1760, 1722, 1219, 997 cm$^{-1}$. HRMS calculated for $C_{28}H_{37}O_{13}$ (M$^+$-OAc): 581.2234, found: 581.2222. $[\alpha]_D^{26}$=+48.95 (c 6.3, CHCl$_3$).

Example 8

DART-C(O)—O-Triclosan

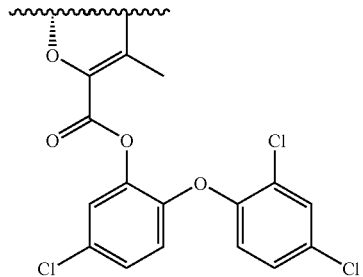

Into a flame-dried 10 mL RBF was charged DART-C(O)—OH (52.7 mg, 0.17 mmol), DCC (101 mg, 0.48 mmol), DMAP (20.9 mg, 0.17 mmol), triclosan (irgsan, 107 mg, 0.37 mmol), and a stir-bar. Dichloromethane (5 mL) was then added and the mixture was stirred overnight at RT. About half the volume of solvent was evaporated and then the residue was purified by flash column chromatography (silica gel, 12.5% ether in petroleum ether). This afforded slightly impure product that was purified further by a second column (silica gel, ethyl acetate/hexanes) to give DART-C(O)—O-triclosan (60.2 mg, 0.010 mmol, 61%). $^1$H NMR (300 MHz, CDCl$_3$): δ 7.4-7.39 (d, J=2 Hz, 1H), 7.28-7.27 (d, J=3 Hz, 1H), 7.19-7.11 (m, 2H), 6.89-6.84 (2s, 2H), 5.65 (s, 1H), 2.43-2.30 (m, 1H), 2.12-1.86 (m, 6H), 1.75-0.98 (m, 12H), 0.97-0.92 (m, 1H). $^{13}$C NMR (75 MHz, CDCl$_3$): δ 160.2, 151.2, 146.7, 141.9, 134.8, 130.3, 129.3, 129.1, 128, 126.9, 126, 124.8, 123.9, 120.5, 120.3, 104.7, 90.2, 77.9, 50.6, 48.4, 37.5, 36.1, 34.1, 28.9, 25.6, 24.3, 20.1, 17.8. IR (thin film): 2929, 1746, 1472, 1259, 1019 cm$^{-1}$. HRMS (FAB$^+$): calculated for C$_{28}$H$_{27}$Cl$_3$O$_7$: 580.0822, found 580.0814. $[α]_D^{27}$=+70.91 (c 7.7, CHCl$_3$)

Example 9

DART-C(O)—NHEt

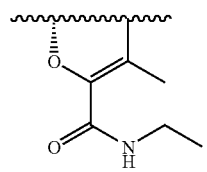

Into a flame-dried 10 mL RBF was charged DART-C(O)—OH (56 mg, 0.18 mmol), 1-(3-dimethylaminopropyl)-3-ethylcarbodiimide hydrochloride, EDC, (54.9 mg, 0.287 mmol), hydroxybenzotriazole, HOBt, (29 mg, 0.214 mmol) and ethylamine hydrochloride (56 mg, 0.687 mmol). Dichloromethane (5 mL) was then added the mixture was stirred and TEA (0.18 mL, 1.2 mmol) was added. The resulting solution was allowed to stir for about 20 hours, and was then quenched by the addition of 10% aqueous hydrochloric acid (3 mL). The mixture was then diluted with water (20 mL) and dichloromethane (20 mL). The aqueous layer was further extracted with dichloromethane (3×20 mL) and the combined organics were washed with saturated aqueous sodium chloride, dried with magnesium sulfate, filtered, and evaporated. The residue was then purified by preparative thin layer chromatography (silica gel, 30% ethyl acetate in hexanes) to give DART-C(O)—NHEt (36.9 mg, 0.11 mmol, 61%). $^1$HNMR (CDCl$_3$, 400 MHz): δ 6.67 (s, 1H), 5.61 (s, 1H), 3.44-3.22 (m, 2H), 2.42 (m, 1H), 2.12 (s, 3H), 2.07-1.99 (m, 2H), 1.96-1.9 (m, 1H), 1.80-1.76 (m, 1H), 1.69-1.65 (m, 1H), 1.57-1.35 (m, 7H), 1.23-1.04 (m, 6H), 0.97-0.96 (d, J=6 Hz, 3H). $^{13}$C NMR (CDCl$_3$, 100 MHz): δ 163.2, 136.6, 116.8, 104.6, 90.3, 78.2, 50.5, 48.2, 37.6, 36.0, 34.1, 33.7, 29, 25.8, 24.4, 20.1, 16.9, 14.8. IR (thin film): 3442, 2929, 1780, 1653, 1512, 1130, 834 cm$^{-1}$. HRMS (FAB$^+$) calculated for C$_{18}$H$_{28}$NO$_5^+$ 338.1968, found 338.1972. $[α]_D^{26}$=+93.73 (c 9.6, CHCl$_3$)

Example 10

DART-C(O)—OMe

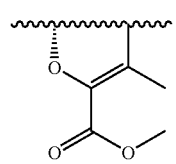

Into a flame-dried 25 mL RBF was charged a stir-bar, DART-C(O)—OH (50 mg, 0.16 mmol) and dichloromethane (10 mL). The flask was immersed in an ice water bath and stirred. After a few minutes N,N-dimethylformamide (1 drop) was added followed by oxalyl chloride (17 μL, 0.19 mmol) and the resulting solution was stirred for approximately 20 minutes. Excess methanol (0.5 mL) was then added and the reaction was stirred for a few minutes. It was then quenched by the addition of saturated aqueous sodium bicarbonate. The aqueous layer was extracted with dichloromethane (3×, 20 mL each) and the combined organics were washed with saturated aqueous sodium chloride, dried with magnesium sulfate, filtered, and evaporated. The residue was then purified by flash column chromatography (silica gel) to give DART-C(O)—OMe (20.6 mg, 0.064 mmol, 40%). $^1$HNMR (CDCl$_3$, 400 MHz): δ 5.69 (s, 1H), 3.82 (s, 3H), 2.45-2.37 (m, 1H), 2.09-1.85 (m, 7H), 1.74-1.44 (m, 8H), 1.29-1.12 (m, 3H), 1.01-0.995 (d, J=6 Hz, 3H). $^{13}$C NMR (CDCl$_3$, 100 MHz): δ 163.6, 135.8, 120.6, 104.7, 90.2, 78.0, 51.9, 50.6, 48.2, 37.5, 36.1, 34.1, 29, 25.7, 24.3, 20.1, 17.6. IR (thin film): 2926, 1722, 1226, 1000 cm$^{-1}$. HRMS (FAB$^+$): calculated for C$_{17}$H$_{24}$O$_6$: 324.1573, found 324.1574. $[α]_D^{25}$=+104.38 (c 2.3, CHCl$_3$)

Example 11

DART-C(O)—O-chol

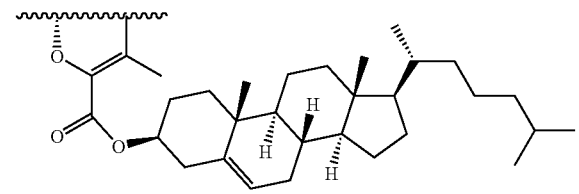

DART-C(O)—OH (63 mg, 0.2 mmol), DMAP (11.7 mg, 0.08 mmol), and cholesterol (88.2 mg, 0.23 mmol) were loaded together with a stir-bar into a flame dried 20 mL RBF. Dichloromethane (10 mL) was then added and the flask was immersed into an ice water bath. After a few minutes of stirring, DCC (43 mg, 0.21 mmol) was added and stirred. After approximately one hour the mixture became cloudy and remained cloudy overnight. The solvent was then evaporated and residue was directly purified by flash column chromatography (silica gel, 20% diethyl ether in petroleum ether) to give DART-C(O)—O—chol (81.6 mg, 0.12 mmol, 60%) as a thin film. $^1$H NMR (CDCl$_3$, 300 MHz): δ 5.66 (s, 1H), 5.38 (s, 1H), 4.74-4.69 (m, 1H), 2.41-2.33 (m, 3H), 2.01-0.82 (m, 57H), 0.67 (s, 3H). $^{13}$C NMR (CDCl$_3$, 75 MHz): δ 162.7, 139.9, 136.4, 122.6, 119.2, 104.5, 90.0, 78.0, 74.7, 56.7, 56.1, 50.1, 50.0, 48.2, 42.3, 39.7, 39.5, 38.1, 37.6, 37.1, 36.7, 36.2, 36.1. HRMS calculated for C$_{43}$H$_{66}$O$_6$Na$^+$: 701.4752, observed: 701.4744.

Example 12

DART-C(O)—O-DaAm

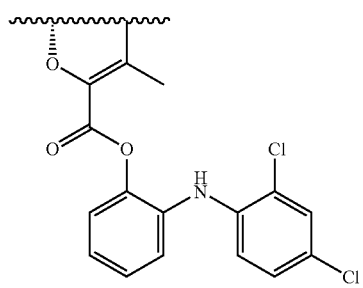

Into a 25 mL flame-dried RBF was loaded a stirbar, DaAmOH (90 mg, 0.35 mmol), DCC (61.4 mg, 0.3 mmol), DMAP (15 mg, 0.12 mmol), and DART-C(O)OH (49.8 mg, 0.16 mmol). Dichloromethane (5 mL) was then added and the mixture was stirred overnight. The solvent was evaporated to about half volume and the residue was purified by flash column chromatography (first column: silica gel, 17% diethyl ether in petroleum ether; second column: silica gel, 14% diethyl ether in petroleum ether) to give DaAm—O—(O)C-DART as an amorphous white solid (33.3 mg, 0.061 mmol, 38%) $^1$H NMR (300 MHz, MeOD): δ 7.38-7.04 (m, 6H), 6.94-6.91 (d, J=9 Hz, 1H), 5.65 (s, 1H), 2.40-2.31 (m, 1H), 2.1-1.88 (m, 7H), 1.75-1.71 (m, 1H), 1.63-1.11 (m, 9H), 1.02-1.00 (d, J=6 Hz, 3H), 0.93-0.86 (m, 1H). $^{13}$C (75 MHz, MeOD): δ 160.9, 143.2, 139.5, 134.9, 133.8, 128.7, 127.2, 126.4, 124.1, 123.6, 123.3, 123.1, 122.6, 122.2, 117.3, 104.5, 90.3, 78, 50.6, 37.2, 35.8, 33.8, 28.6, 24.5, 24.1, 19.1, 16.5. IR (thin film): 3410, 2928, 1743, 1522, 1024, 737 cm$^{-1}$. HRMS (FAB$^+$) calculated for $C_{28}H_{29}Cl_2NO_6$: 545.1372, found 545.1373.

Example 13

DART-C(O)—O-cit

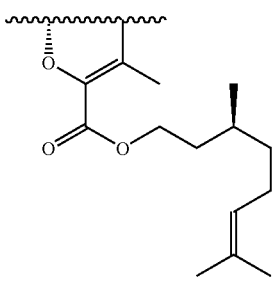

DART-C(O)—OH (64 mg, 0.22 mmol) was placed in a 10 mL RBF with a stir-bar and dissolved, with stirring, in DMF. Citronellyl bromide (46 μL, 0.231 mmol) was then added followed by the addition of NaH (11 mg, 60% dispersion in mineral oil, 0.26 mmol). After approximately 30 minutes of vigorous stirring, a pale yellow color was seen and a solid or gel appeared to have formed during the reaction. After stirring overnight, the mixture was portioned between diethyl ether (50 mL) and water (50 mL). The organic layer was then washed with 3M NaOH (20 mL) and finally saturated aqueous sodium chloride. It was dried over magnesium sulfate, filtered, and evaporated. The residue was purified by column chromatography (silica gel, 25% diethyl ether in petroleum ether) to give the product as a film (29 mg, 29%). $^1$H NMR (CDCl$_3$, 400 MHz): δ 5.682 ppm (s, 1H), 5.13-5.08 (m, 1H), 4.32-4.23 (m, 2H), 2.44-2.37 (m, 1H), 2.08-1.11 (m, 29H, including 2 s, 1.435 and 2.051, 3H each), 1.01-0.94 (m, 6H, including 2d, 3H, 0.96-0.94, J=6 Hz, and 1.1-1, J=6 Hz). $^{13}$C NMR (CDCl$_3$, 100 MHz): δ 163.29, 136.17, 131.2, 124.63, 119.64, 104.56, 90.04, 78.01, 63.43, 20.59, 48.17, 37.54, 37.09, 36.12, 35.36, 34.13, 29.66, 28.84, 25.67, 25.61, 25.41, 24.31, 20.08, 19.40, 17.60. IR (thin film) 3428.1, 2927.4, 1717.2, 1266.7, and 1122.3 cm$^{-1}$. HRMS: calculated for $C_{26}H_{40}O_6Na^+$: 471.2717, observed 471.2705. $[α]_D^{27}$=+28.66 (c 14.5, CHCl$_3$)

Example 14

DART-ald

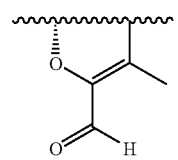

DART-C(O)—OH (0.523 g, 1.5 mmol) was dissolved, with stirring, in acetonitrile (25 mL) with 4 Å molecular sieve (2 g, powdered) in a 200 mL RBF. Methyl trifluoromethanesulfonate (0.32 mL, 2.85 mmol) was then added via syringe and the suspension was stirred, open to the air, for 30 minutes. The solvent was evaporated and the residue was taken up in methanol (40 mL), immersed in an ice water bath, and stirred. After a couple of minutes, sodium borohydride (0.28 g, 7.5 mmol) was added and the mixture stirred at 0° C. for 15 minutes followed by RT for 15 minutes. The flask was then replaced in the ice water bath and was quenched with acetone. The mixture was filtered through Celite® and evaporated. The residue was taken up in acetonitrile (20 mL) and mercury (II) chloride (0.51 g, 2.1 mmol) was added, followed by water (3 mL). The mixture became thick. After one hour, the mixture was filtered through Celite® and the Celite® was washed with dichloromethane. The solution was further diluted with dichloromethane (100 mL). The organic layer was then washed with 20% aqueous potassium iodide, water, and saturated aqueous sodium chloride. The organics were then dried over magnesium sulfate, filtered, and evaporated. The residue was purified by flash column chromatography (silica gel, 50% diethyl ether in petroleum ether) to give the product DART-ald as a white solid (270 mg, 61%). $^1$H NMR (CDCl$_3$, 400 MHz): δ 9.747 (s, 1H), 5.669 (s, 1H), 2.40-2.32 (m, 1H), 2.08-2.00 (m, 5H), 1.94-1.87 (m, 2H), 1.74-1.7 (m, 1H), 1.57-1.40 (m, 6H), 1.36-1.12 (m, 2H), 0.98-0.97 (d, 3H, J=6 Hz). $^{13}$C NMR (CDCl$_3$, 100 MHz): δ 184.3, 142.9, 126.6, 104.8, 90.1, 781.0, 50.6, 47.9, 37.4, 36.1, 34.0, 28.8, 25.7, 24.2, 20.0, 14.8.

Example 15

DART-C(O)—OH

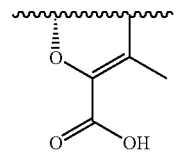

DART-ald (1.313 g, 4.46 mmol), 3-methyl 2-butene (18 mL) were placed together with a stir-bar, and t-BuOH (10 mL) in a 100 mL RBF. A solution of sodium chlorite (2.47 g, 27.2 mmol), and sodium phosphate (3.34 g, 27.2 mmol) in water (10 mL) was added. After about 90 minutes, the reaction was quenched with 0.5M hydrochloric acid (50 mL) and then extracted with dichloromethane (3×, 50 mL each). The organic layers were combined, washed with saturated aqueous sodium chloride, dried over magnesium sulfate, filtered, and evaporated. The residue was purified with flash column chromatography (silica gel, 40% diethyl ether in petroleum ether followed by 100% ethyl acetate) to give product DART-C(O)—OH as a white solid (1.033 g, 75%). $^1$H NMR (CDCl$_3$): δ 5.67 (s, 1H), 2.40-2.32 (m, 1H), 2.08 (s, 3H), 2.05-1.99 (m, 2H) 1.94-1.85 (m, 2H), 1.71-1.67 (m, 1H), 1.52-1.38 (m, 6H), 1.25-1.08 (m, 2H), 0.97-0.96 (d, J=6.0 Hz, 2H)(COOH$^1$H was not observed). $^{13}$C NMR (CDCl$_3$): δ 17.568, 20.049, 24.246, 25.635, 28.763, 34.029, 35.991, 37.497, 48.424, 50.424, 78.021, 90.517, 104.926, 123.373, 134.312, 164.3, 134.3, 123.4, 104.9, 90.5, 78.0, 50.4, 48.4, 37.5, 36, 34.0, 28.8, 25.6, 24.3, 20.0, 17.6.

Example 16 deoxy-DART-thiaz

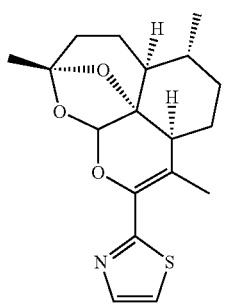

A flame-dried 10 mL RBF was loaded with a stir-bar and deoxy-ART (65.1 mg, 0.24 mmol). THF (2 mL) was added and the mixture was stirred and immersed into a dry ice/acetone bath. Meanwhile, in a separate flame-dried 10 mL RBF was loaded a stir-bar and diethyl ether (3 mL). Then 2-bromothiazole (0.03 mL, 0.34 mmol) was added and the system was immersed in a dry ice/acetone bath. After cooling, n-BuLi (0.2 mL, 1.6 M in hexane, 0.32 mmol) was added and the mixture was stirred for 50 minutes. After 50 minutes, the solution of deoxy-ART in THF was added, via canula, and the mixture stirred for 2.5 hr. The temperature was increased to −60° C. and stirred for 1.5 hours after which time acetic anhydride (0.17 mL, 1.63 mmol) was added and the mixture was allowed to stir at RT overnight. Then BF$_3$-etherate (0.58 mL, 4.6 mmol) was added and the mixture was stirred for a few hours. The reaction mixture was diluted with 50 mL dichloromethane and the organic layer was washed with saturated aqueous sodium bicarbonate (3×25 mL) and saturated aqueous sodium chloride, dried over magnesium sulfate, filtered, and evaporated. The residue was purified by prep TLC (silica gel, 17% ethyl acetate in hexanes) to give deoxy-DART-thiaz (12.5 mg, 0.037 mmol, 16%) as an amorphous off-white solid. $^1$H NMR (CDCl$_3$, 400 MHz): δ 7.84-7.83 (d, J=3 Hz, 1H), 7.28-7.27 (d, J=3 Hz, 1H), 5.69 (s, 1H), 2.34 (s, 3H), 2.20-2.16 (m, 1H), 1.94-1.86 (m, 2H), 1.82-1.73 (m, 2H), 1.14-1.66 (m, 12H), 0.98-0.96 (m, 4H). $^{13}$C NMR (CDCl$_3$, 100 MHz): δ 166, 143.2, 137.3, 118.2, 117.9, 108.1, 97.1, 84.2, 45.2, 44.8, 35.4, 34.3, 34.1, 26, 24.1, 218, 18.6, 17.9. IR (thin film): 2925, 1084, 876. $[α]_D^{25}$=−175.26 (c 1.0, CHCl$_3$)

Optimized Procedure for Deoxy-DART-thiaz

A flame-dried 2 mL RBF was loaded with a stir-bar and DART-thiaz (65.1 mg, 0.24 mmol). Glacial acetic acid (1 mL) was added while stirring at RT. Meanwhile, in a separate flame-dried 10 mL RBF was charged zinc dust (26.2 mg, 0.42 mmol) under argon. The zinc dust was washed successively with 5% aqueous hydrochloric acid (5 mL), deionized water (5 mL), 200-proof ethanol (5 mL), and diethyl ether (5 mL) with each washing being decanted off the zinc and removed with a syringe. The "activated" zinc dust was dried on a high vacuum line for approximately 15 minutes. The "activated" zinc dust was charged to the 2 mL flask in one portion. The reaction was stirred at RT for two hours. Afterwards the reaction was filtered through Celite®-545 and added to a separatory funnel containing chloroform (5 mL) and water (2.5 mL). The Celite® was rinsed with chloroform (2.5 mL) which was added to the separatory funnel. The organic layer was washed successively with saturated aqueous sodium bicarbonate (3×2.5 mL), water (3×2.5 mL), saturated aqueous sodium chloride (3×2.5 mL), dried over magnesium sulfate, and concentrated, in vacuo, at 40° C. to afford a light yellow solid (21 mg). The solid was purified by flash column chromatography (3.2 grams of silica gel, packed with 100% hexanes, eluted with 5% ethyl acetate in hexanes) to give deoxy-DART-thiaz (14.1 mg, 0.042 mmol, 73.8%) as an amorphous white solid.

Example 17

ART-thiaz

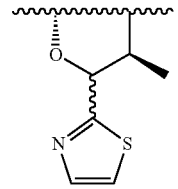

BF$_3$ etherate (0.049 mL, 0.39 mmol) was added to a cold (−40° C.) stirred solution of 10-β-benzoate (0.050 g, 0.13 mmol) and thiazole (0.046 mL, 0.65 mmol) in dichloromethane (1.25 mL). After 4 hours at this temperature, n-BuLi (0.258 mL, 2.5M in hexanes) was added at −78° C. to a solution of thiazole (0.046 mL, 0.65 mmol) in 0.5 mL of dichloromethane in a separate flask. The contents of this flask were then added, via cannula, into the original reaction mixture at −78° C. The reaction stirred for an additional 15 minutes after which it was quenched with saturated aqueous sodium bicarbonate solution, and the reaction mixture was extracted with dichloromethane (3×3 mL). The organic layer was washed with saturated aqueous sodium bicarbonate followed by saturated aqueous sodium chloride, dried over magnesium sulfate, filtered, and concentrated, in vacuo, at 30° C. The residue was purified by flash column chromatography (silica gel, 25% ethyl acetate in hexanes) to give ART-thiaz as an impure oil.

Example 18

Deoxy-ART-PrOH

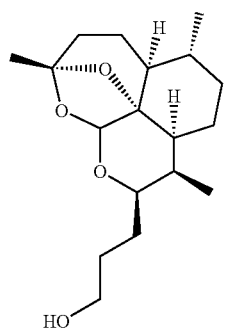

Deoxy-ART-allyl (0.244 g, 0.834 mmol) was loaded together with a stir-bar into an oven-dried 100 mL RBF. The system was placed under an argon balloon and THF (20 mL) was added. The system was then immersed in an ice water bath and after cooling, the BH$_3$.DMS solution (0.5 mL of a 2M sol in diethyl ether, 1 mmol) was added rapidly via syringe. After approximately one hour, the TLC showed consumption of the starting material. The mixture was then stirred an additional three hours and a suspension of NaBO$_3$.H$_2$O (0.67 g, 4.34 mmol) in H$_2$O (20 mL) was added resulting in a vigorous liberation of gas. The reaction mixture was allowed to stir for ~23 hours and was portioned between dichloromethane (50 mL) and water (50 mL). The aqueous layer was extracted with dichloromethane (2×, 50 mL each) and the organic layers were combined, washed with water (50 mL) and saturated aqueous sodium chloride, dried with magnesium sulfate, filtered, and evaporated. The residue was purified by flash column chromatography (silica gel, 17% petroleum ether in diethyl ether) to give the product deoxy-ART-PrOH as a clear, pale yellow oil that solidified to a wax-like white solid on long standing (0.186 g, 72%). $^1$H NMR (CDCl$_3$): δ 5.21 (s, 1H) 4.02-4.08 (m, 1H) 3.57-3.61 (t, 2H, J=6.1 Hz) 2.44 (s, 1H) 2.11-2.16 (m, 1H) 1.36-1.92 (m, 13H, including a singlet at 1.45, 3H) 1.09-1.24 (m, 4H) 0.8-0.95 (m, 7H). $^{13}$C NMR (CDCl$_3$): δ 107, 97.2, 82.5, 68.5, 62.4, 45.3, 40.3, 35.5, 34.53, 34.49, 30.0, 29.8, 27.8, 25.2, 23.6, 22.1, 18.8, 12.9. IR (thin film): 3442.5, 2950.1, 1457.2, 1100.6, and 995.2 cm$^{-1}$. HRMS FAB$^+$ calculated for C$_{18}$H$_{31}$O$_4$$^+$: 311.2222; found: 311.2200. [α]D$^{26}$=−103.02 (c 6.51, CHCl$_3$)

Optimized Procedure for Deoxy-ART-PrOH

A flame-dried 0.5 dram vial was loaded with a stir-bar and ART-PrOH (10.0 mg, 0.03 mmol). Glacial acetic acid (0.5 mL) was added while stirring at RT. Meanwhile, in a separate flame-dried 10 mL RBF was charged zinc dust (14.0 mg, 0.21 mmol) under argon. The zinc dust was washed successively with 5% aqueous hydrochloric acid (5 mL), deionized water (5 mL), 200-proof ethanol (5 mL), and diethyl ether (5 mL) with each washing being decanted off the zinc and removed with a syringe. The "activated" zinc dust was dried on a high vacuum line for approximately 15 minutes. The "activated" zinc dust was charged to the vial in one portion. The reaction was stirred at RT for two hours. Afterwards the reaction was filtered through Celite®-545 and added to a separatory funnel containing ethyl acetate (5 mL) and water (5 mL). The Celite® was rinsed with ethyl acetate (5 mL) which was added to the separatory funnel. The organic layer was washed successively with saturated aqueous sodium bicarbonate (3×5 mL), water (3×5 mL), saturated aqueous sodium chloride (3×5 mL), dried over magnesium sulfate, and concentrated, in vacuo, at 40° C. to afford a colorless oil (11.7 mg). The oil was purified by flash column chromatography (4.9 grams of silica gel, packed with 100% hexanes, eluted with 30% ethyl acetate in hexanes) to give deoxy-ART-PrOH (4.5 mg, 0.01 mmol, 47.4%) as a colorless oil.

Example 19

Deoxy-ART-pyrrole

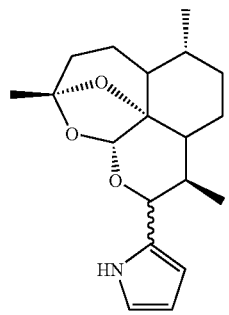

A flame-dried 2 mL RBF was loaded with a stir-bar and ART-pyrrole (25.0 mg, 0.075 mmol). Glacial acetic acid (0.5 mL) was added while stirring at RT. Meanwhile, in a separate flame-dried 10 mL RBF was charged zinc dust (20.0 mg, 0.30 mmol) under argon.

The zinc dust was washed successively with 5% aqueous hydrochloric acid (2.5 mL), deionized water (2.5 mL), 200-proof ethanol (2.5 mL), and diethyl ether (2.5 mL) with each washing being decanted off the zinc and removed with a syringe. The "activated" zinc dust was dried on a high vacuum line for approximately 15 minutes. The "activated" zinc dust was charged to the 2 mL flask in one portion. The reaction was stirred at RT for two hours. Afterwards the reaction was filtered through Celite®-545 and added to a separatory funnel containing chloroform (2.5 mL) and water (1.25 mL). The Celite® was rinsed with chloroform (2.5 mL) which was added to the separatory funnel. The organic layer was washed successively with saturated aqueous sodium bicarbonate (3×2.5 mL), water (3×2.5 mL), saturated aqueous sodium chloride (3×2.5 mL), dried over magnesium sulfate, and concentrated in vacuo to afford a light yellow solid. The solid was purified by flash column chromatography (15% ethyl acetate in hexanes) to give deoxy-ART-pyrrole (12.0 mg, 0.038 mmol, 50%) as an amorphous white solid. Characteristic NMR peaks include: $^1$H NMR (CDCl$_3$, 400 MHz): δ 8.60 (br. s, 1H), 6.73 (m, 1H), 6.04 (m, 2H), 5.42 (s, 1H), 4.55 (d, J=10 Hz, 1H), 2.48 (m, 1H). $^{13}$C NMR shows peaks at 91.9 and 60.2 in ART-pyrrole shift to 96.1 and 72.9, respectively, in deoxy-ART-pyrrole.

REFERENCES

1. Bachmann, S., J. Schroder, C. Bottmer, E. F., Torrey, and R. H. Yolken. 2005. Psychopathology in first-episode schizophrenia and antibodies to *Toxoplasma gondii*. Psychopathol. 38(2):87-90.
2. Berens, R. L., E. C. Krug, P. B. Nash, and T. J. Curiel. 1998. Selection and characterization of *Toxoplasma gondii* mutants resistant to artemisinin. J. Infect. Dis. 177:1128-1131.

3. Brossi, A., B. Venugopalan, L. Dominguez Gerpe, H. J. C. Yeh, J. L. Flippen-Anderson, P. Bucks, X. D. Luo, W. Milhous, and W. Peters. 1988. Arteether, a new antimalarial drug: Synthesis and antimalarial properties. J. Med. Chem. 31(3):645-650.
4. Chang, H. R., C. W. Jefford, and J.-C. Pechére. 1989. In vitro effects of three new 1,2,4-trioxanes (pentatroxane, thiahexatroxane, and hexatroxanone) on *Toxoplasma gondii*. Antimicrob. Agents Chemother. 33(10):1748-1752.
5. Dobrowolski, J. M., and L. D. Sibley. 1996. *Toxoplasma* invasion of mammalian cells is powered by the actin cytoskeleton of the parasite. Cell. 84(6):933-939.
6. Georgiev, V. S. 1994. Management of toxoplasmosis. Drugs. 48(2):179-188.
7. Holfels, E., J. McAuley, D. Mack, W. K. Milhous, and R. McLeod. 1994. In vitro effects of artemisinin ether, cycloguanil hydrochloride (alone and in combination with sulfadiazine), quinine sulfate, mefloquine, primaquine phosphate, trifluoperazine hydrochloride, and verapamil on *Toxoplasma gondii*. Antimicrob. Agents Chemother. 38(6):1392-1396.
8. Huynh, M.-H., K. E. Rabenau, J. M. Harper, W. L. Beatty, L. D. Sibley, and V. B. Carruthers. 2003. Rapid invasion of host cells by *Toxoplasma* requires secretion of the MIC2-M2AP adhesive protein complex. EMBO J. 22(9):2082-2090.
9. Jones-Brando, L., J. D'Angelo, G. H. Posner, and R. Yolken. 2006. In vitro inhibition of *Toxoplasma gondii* by four new derivatives of artemisinin. Antimicrob. Agents Chemother. 50(12):4206-4208.
10. Jones-Brando, L., E. F. Torrey, and R. Yolken. 2003. Drugs used in the treatment of schizophrenia and bipolar disorder inhibit the replication of *Toxoplasma gondii*. Schizophr. Res. 62:237-244.
11. Lin A. J., D. L. Klayman, and W. K. Milhous. 1987. Antimalarial activity of new water-soluble dihydroartemisinin derivatives. J. Med. Chem. 30:2147-2150.
12. O'Neill P. M., and G. H. Posner. 2004. A medicinal chemistry perspective on artemisinin and related endoperoxides. J. Med. Chem. 47:2945-2964.
13. Ou-Yang, K., E. C. Krug, J. J. Marr, and R. L. Berens. 1990 Inhibition of growth of *Toxoplasma gondii* by Qinghaosu and derivatives. Antimicrob. Agents Chemother. 34(10):1961-1965.
14. Silverman, J. A., M. L. Hayes, B. J. Luft, and K. A. Joiner. 1997. Characterization of anti-Toxoplasma activity of SDZ 215-918, a cyclosporin derivative lacking immunosuppressive and peptidyl-prolyl-isomerase-inhibiting activity: possible role of a P glycoprotein in *Toxoplasma* physiology. Antimicrob. Agents Chemother. 41(9):1859-1866.
15. Tenter, A. M., A. R. Heckeroth, and L. M. Weiss. 2000. *Toxoplasma gondii*: from animals to humans. Intl. J. Parasitol. 30:1217-1258.
16. Torrey E F, Bartko J J, Lun Z R, Yolken R H. 2007. Antibodies to *Toxoplasma gondii* in patients with schizophrenia: a meta-analysis. Schizophr Bull. 33(3):729-736.
17. Yolken, R. H., S. Bachmann, I. Ruslanova, E. Lillehoj, G. Ford, E. F. Torrey, and J. Schröder. 2001. Antibodies to *Toxoplasma gondii* in individuals with first-episode schizophrenia. Clin. Infect. Dis. 32(5):842-844.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound having formula I:

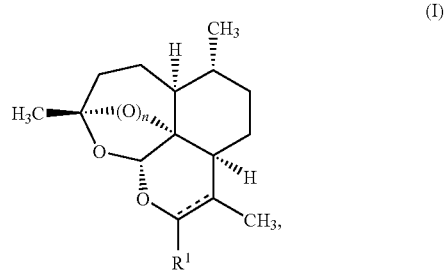

or an enantiomer, diastereomer, racemate or pharmaceutically acceptable salt or solvate thereof, wherein:
- - - - - is a double bond;
n is independently an integer from 1 to 2;
$R^1$ is independently substituted or unsubstituted alkyl, substituted or unsubstituted aryl, substituted or unsubstituted arylalkyl, substituted or unsubstituted heteroaryl, substituted or unsubstituted heteroarylalkyl, —$(CH_2)_jR^2$, —$(CH_2)_jO(CH_2)_kR^2$, —$(CH_2)_jC(O)(CH_2)_kR^2$, —$(CH_2)_jOC(O)(CH_2)_kR^2$, —$(CH_2)_jC(O)O(CH_2)_kR^2$, —$(CH_2)_jNR^3R^4$, —$(CH_2)_jC(O)(CH_2)_kNR^3R^4$, —$(CH_2)_jNR^5C(O)(CH_2)_kR^2$, —$(CH_2)_jOC(O)(CH_2)_kNR^3R^4$, —$(CH_2)_jNR^5C(O)(CH_2)_kOR^2$, —$(CH_2)_jNR^5C(O)(CH_2)_kNR^3R^4$, wherein each j and each k is independently an integer from 0 to 6; and m is independently an integer from 0 to 2;
$R^2$ is independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, substituted or unsubstituted (aryl or heteroaryl)-X-(aryl or heteroaryl) wherein X is O, S, NH or N($C_1$-$C_6$)alkyl, cholesterol, or a substituted or unsubstituted monosaccharide, and wherein each $R^2$ is optionally independently substituted with 1 to 5 $R^{10}$ groups;
$R^3$, $R^4$, and $R^5$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^3$, $R^4$, and $R^5$, are each optionally independently substituted with 1 to 5 $R^{10}$ groups, or
$R^3$ and $R^4$, together with the N atom to which they are attached, form substituted or unsubstituted heterocycloalkyl, or substituted or unsubstituted heteroaryl, wherein substituted or unsubstituted heterocycloalkyl, and substituted or unsubstituted heteroaryl are each optionally independently substituted with 1 to 5 $R^{10}$ groups, and $R^5$ is as described above; and
each $R^{10}$ is independently hydrogen, halogen, hydroxyl, amino, aminoalkyl, aminodialkyl, cyano, nitro, alkyl, —O-alkyl, —S-alkyl, perfluoroalkyl, —O— perfluoroalkyl, oxo, acetyl, or -benzyl, wherein:

$R^2$ is not hydrogen, unsubstituted phenyl, or n-Bu when $R^1$ is —$(CH_2)_jC(O)(CH_2)_kR^2$; ----- is a double bond; n is 2; and j and k are each independently 0; and $R^1$ is not unsubstituted thiazole or unsubstituted benthiazole when ----- is a double bond; and n is 2.

2. The compound of claim 1, wherein:
$R^1$ is independently substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl.

3. The compound of claim 1, wherein
$R^1$ is independently —$(CH_2)_jC(O)(CH_2)_kR^2$, —$(CH_2)_jOC(O)(CH_2)_kR^2$, —$(CH_2)_jC(O)O(CH_2)_kR^2$, or —$(CH_2)_jC(O)(CH_2)_kNR^3R^4$; and $R^2$ is independently hydrogen, substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl; and $R^3$ and $R^4$ are each independently hydrogen, substituted or unsubstituted alkyl, substituted or unsubstituted phenyl, substituted or unsubstituted benzyl, or $R^3$ and $R^4$, together with the N atom to which they are attached, form substituted or unsubstituted pyrrolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl.

4. The compound of claim 3, wherein:
$R^1$ is independently —$C(O)R^2$, —$OC(O)R^2$, —$C(O)OR^2$, or —$C(O)NR^3R^4$;

$R^2$ is independently hydrogen, substituted or unsubstituted alkyl, or substituted or unsubstituted phenyl; and $R^3$ and $R^4$ are each independently hydrogen, or substituted or unsubstituted alkyl.

5. The compound of claim 1, wherein:
$R^1$ is independently —$(CH_2)_jC(O)O(CH_2)_kR^2$; and $R^2$ is independently substituted or unsubstituted glucose, substituted or unsubstituted galactose, substituted or unsubstituted mannose, substituted or unsubstituted fructose.

6. The compound of claim 5, wherein:
$R^1$ is independently —$C(O)OR^2$; and $R^2$ is tetraacetyl α-D glucopyranose, tetraacetyl β-D glucopyranose, tetraacetyl α-D galactose, tetraacetyl β-D galactose, tetraacetyl α-D mannose, tetraacetyl β-D mannose, tetraacetyl α-D fructose, or tetraacetyl β-D fructose.

7. The compound of claim 1, wherein the compound of formula I, has formula II:

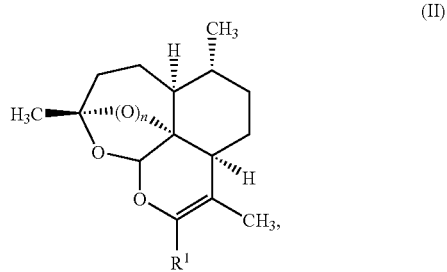

wherein:
n is 1;
$R^1$ is independently substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, —$(CH_2)_jC(O)(CH_2)_kR^2$, —$(CH_2)_jOC(O)(CH_2)_kR^2$, —$(CH_2)_jC(O)O(CH_2)_kR^2$, or —$(CH_2)_jC(O)(CH_2)_kNR^3R^4$;

$R^2$ is independently hydrogen, substituted or unsubstituted alkyl, substituted or unsubstituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted or unsubstituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted or unsubstituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, or substituted or unsubstituted phenyl-NH-phenyl; and $R^3$ and $R^4$ are each independently hydrogen, substituted or unsubstituted alkyl, substituted or unsubstituted phenyl, substituted or unsubstituted benzyl, or $R^3$ and $R^4$, together with the N atom to which they are attached, form substituted or unsubstituted pyrrolidinyl, substituted or unsubstituted piperidinyl, substituted or unsubstituted piperazinyl, substituted or unsubstituted morpholinyl, substituted or unsubstituted thiomorpholinyl, substituted or unsubstituted pyrrolyl, or substituted or unsubstituted imidazolyl.

8. The compound of claim 7, wherein:

$R^1$ is independently —$C(O)R^2$, —$OC(O)R^2$, —$C(O)OR^2$, or —$C(O)NR^3R^4$;

$R^2$ is independently hydrogen, substituted or unsubstituted alkyl, or substituted or unsubstituted phenyl; and $R^3$ and $R^4$ are each independently hydrogen, or substituted or unsubstituted alkyl.

9. The compound of claim 8, wherein:

$R^1$ is independently —$(CH_2)_jC(O)O(CH_2)_kR^2$; and $R^2$ is independently substituted or unsubstituted glucose, substituted or unsubstituted galactose, substituted or unsubstituted mannose, substituted or unsubstituted fructose.

10. The compound of claim 9, wherein:

$R^1$ is independently —$C(O)OR^2$; and $R^2$ is tetraacetyl α-D glucopyranose, tetraacetyl β-D glucopyranose, tetraacetyl α-D galactose, tetraacetyl β-D galactose, tetraacetyl α-D mannose, tetraacetyl β-D mannose, tetraacetyl α-D fructose, or tetraacetyl β-D fructose.

11. The compound of claim 1, having formula:

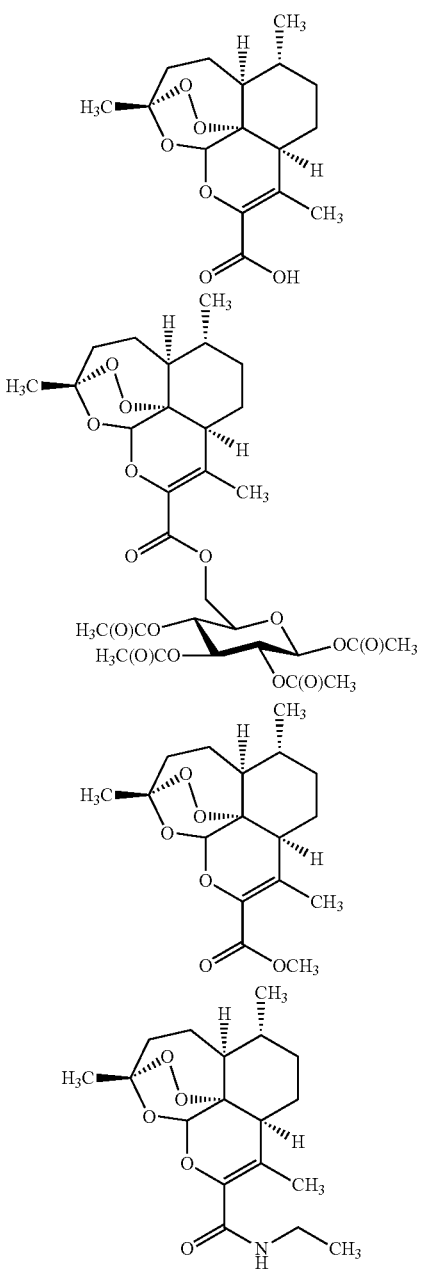

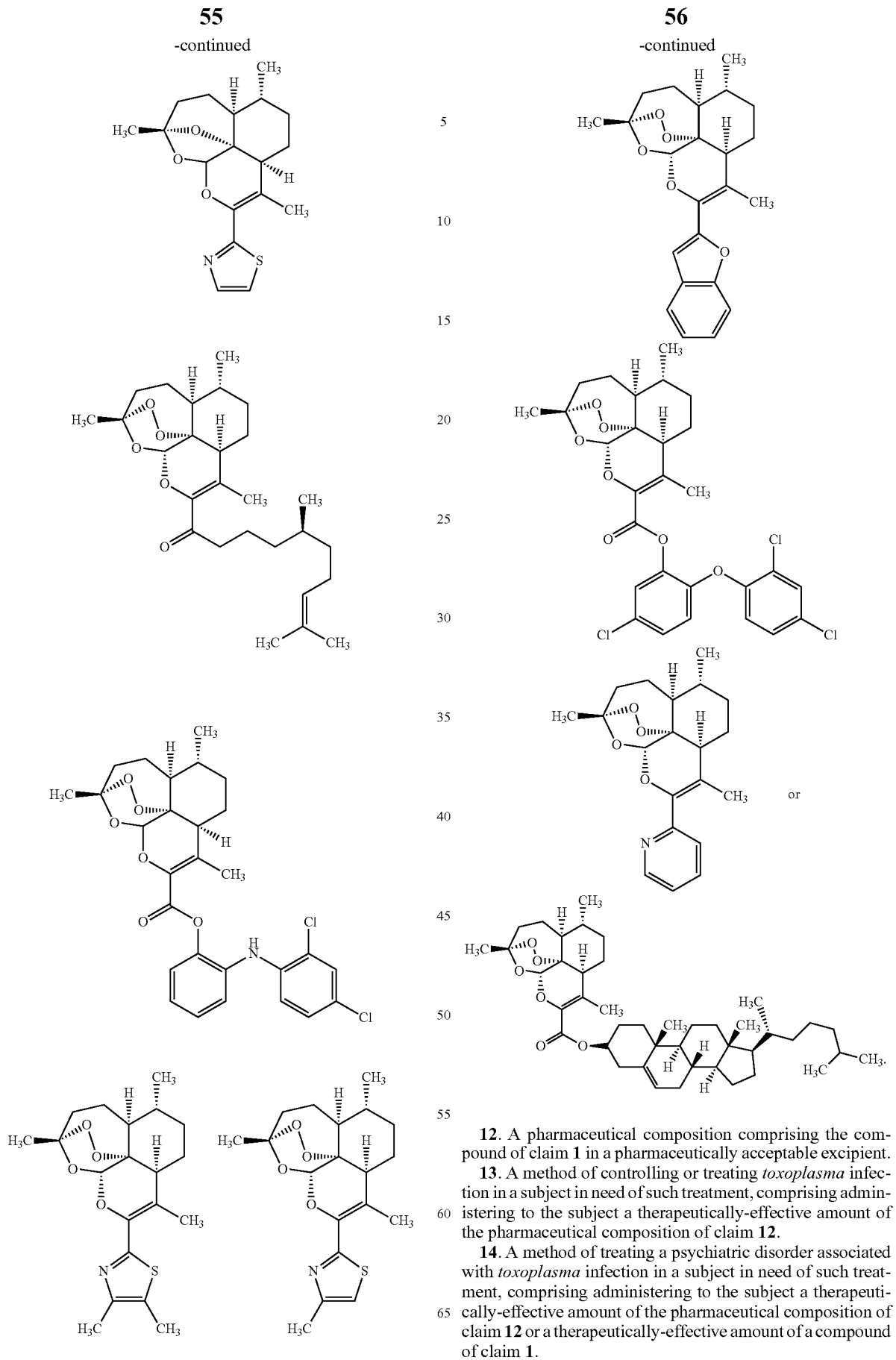

12. A pharmaceutical composition comprising the compound of claim 1 in a pharmaceutically acceptable excipient.

13. A method of controlling or treating *toxoplasma* infection in a subject in need of such treatment, comprising administering to the subject a therapeutically-effective amount of the pharmaceutical composition of claim 12.

14. A method of treating a psychiatric disorder associated with *toxoplasma* infection in a subject in need of such treatment, comprising administering to the subject a therapeutically-effective amount of the pharmaceutical composition of claim 12 or a therapeutically-effective amount of a compound of claim 1.

15. The method of claim 14, wherein the psychiatric disorder is schizophrenia.

16. A method of treating a psychiatric disorder associated with *toxoplasma* infection in a subject in need of such treatment, comprising administering to the subject a therapeutically-effective amount of a pharmaceutical composition, comprising a compound of formula I of claim 1, in combination with one or more antipsychotic drugs selected from chlorpromazine (Thorazine), haloperidol (Haldol), fluphenazine (Prolixin), thiothixene (Navane), trifluoperazine (Stelazine), perphenazine (Trilafon), and thioridazine (Mellaril), clozapine (Clozaril), risperidone (Risperdal), olanzapine (Zyprexa), quetiapine (Seroquel), ziprasidone (Geodon), and aripiprazole (Abilify), in a pharmaceutically acceptable excipient.

17. A method of preparing a compound of formula I, the method comprising the steps of converting the compound of formula IV to the compound of formula I:

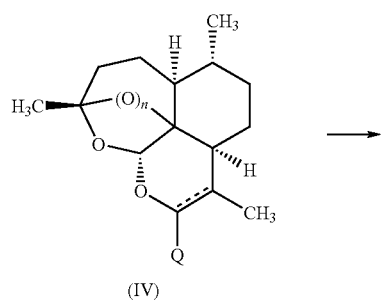

(IV)

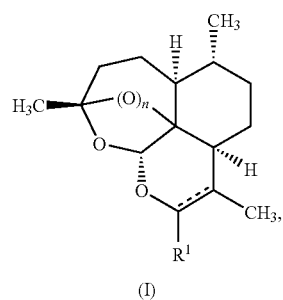

(I)

wherein:
- - - - - - is a single or a double bond;
n is independently an integer from 1 to 2;
Q is independently oxo, —(CH$_2$)$_t$OH or —C(O)OH, wherein each t is independently an integer from 1 to 6; and
R$^1$ is independently substituted or unsubstituted alkyl, substituted or unsubstituted aryl, substituted or unsubstituted arylalkyl, substituted or unsubstituted heteroaryl, substituted or unsubstituted heteroarylalkyl, —(CH$_2$)$_j$R$^2$, —(CH$_2$)$_j$—O—(CH$_2$)$_k$R$^2$, —(CH$_2$)$_j$C(O)(CH$_2$)$_k$R$^2$, —(CH$_2$)$_j$OC(O)(CH$_2$)$_k$R$^2$, —(CH$_2$)$_j$C(O)O(CH$_2$)$_k$R$^2$, —(CH$_2$)$_j$NR$^3$R$^4$, —(CH$_2$)$_j$C(O)(CH$_2$)$_k$NR$^3$R$^4$, —(CH$_2$)$_j$NR$^5$C(O)(CH$_2$)$_k$R$^2$, —(CH$_2$)$_j$OC(O)(CH$_2$)$_k$NR$^3$R$^4$, —(CH$_2$)$_j$NR$^5$C(O)(CH$_2$)$_k$OR$^2$, —(CH$_2$)$_j$NR$^5$C(O)(CH$_2$)$_k$NR$^3$R$^4$, wherein each j and each k is independently an integer from 0 to 6; and m is independently an integer from 0 to 2;
R$^2$ is independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, substituted or unsubstituted (aryl or heteroaryl)-X-(aryl or heteroaryl) wherein X is O, S, NH or N(C$_1$-C$_6$)alkyl, or a substituted or unsubstituted monosaccharide, and wherein each R$^2$ is optionally independently substituted with 1 to 5 R$^{10}$ groups;

R$^3$, R$^4$, and R$^5$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein R$^3$, R$^4$, and R$^5$, are each optionally independently substituted with 1 to 5 R$^{10}$ groups, or R$^3$ and R$^4$, together with the N atom to which they are attached, form substituted or unsubstituted heterocycloalkyl, or substituted or unsubstituted heteroaryl, wherein substituted or unsubstituted heterocycloalkyl, and substituted or unsubstituted heteroaryl are each optionally independently substituted with 1 to 5 R$^{10}$ groups, and R$^5$ is as described above; and each R$^{10}$ is independently hydrogen, halogen, hydroxyl, amino, aminoalkyl, aminodialkyl, cyano, nitro, alkyl, —O-alkyl, —S-alkyl, perfluoroalkyl, —O— perfluoroalkyl, oxo, acetyl, or -benzyl.

18. The compound of claim 1, prepared by a method comprising converting a compound of formula IV to a compound of formula I:

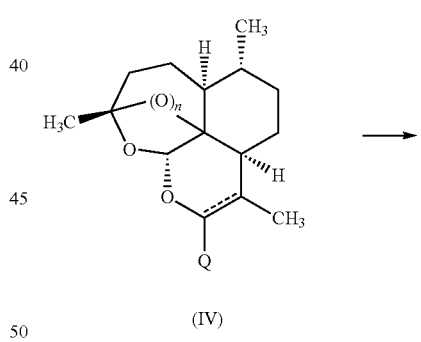

(IV)

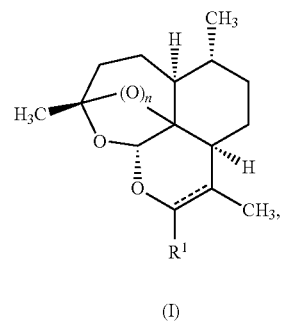

(I)

wherein:
Q is independently oxo, —(CH$_2$)$_t$OH or —C(O)OH; and
each t is independently an integer from 1 to 6.

19. The compound of claim 1, wherein the compound has formula II, wherein:

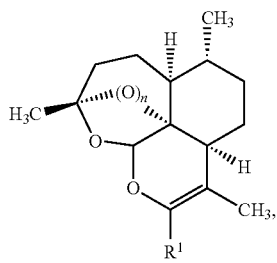

(II)

n is 2; and
R$^1$ is independently substituted alkyl, unsubstituted $C_1$-$C_3$ or $C_5$-$C_{12}$ straight chain alkyl, unsubstituted branched alkyl, substituted phenyl, substituted or unsubstituted naphthyl, substituted or unsubstituted biphenyl, substituted or unsubstituted benzyl, substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted isoxazolyl, substituted or unsubstituted 1,2,4-oxadiazolyl, substituted or unsubstituted 1,3,4-oxadiazolyl, substituted or unsubstituted tetrazolyl, substituted thiazolyl, substituted or unsubstituted isothiazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted indolyl, substituted or unsubstituted indazolyl, substituted or unsubstituted benzofuryl, substituted or unsubstituted benzothienyl, substituted or unsubstituted benzopyrazolyl, substituted or unsubstituted benzimidazolyl, substituted or unsubstituted benzoxazolyl, substituted or unsubstituted benzisoxazolyl, substituted benzothiazolyl, substituted or unsubstituted benzisothiazolyl, substituted or unsubstituted benzotriazolyl, substituted or unsubstituted quinolinyl, substituted or unsubstituted isoquinolinyl, substituted or unsubstituted phthalazinyl, substituted or unsubstituted quinazolinyl, or substituted or unsubstituted quinoxalinyl, —(CH$_2$)$_j$OC(O)(CH$_2$)$_k$R$^2$, —(CH$_2$)$_j$C(O)O(CH$_2$)$_k$R$^2$, or —(CH$_2$)$_j$C(O)(CH$_2$)$_k$NR$^3$R$^4$.

20. The compound of claim 1, wherein the compound, has formula II:

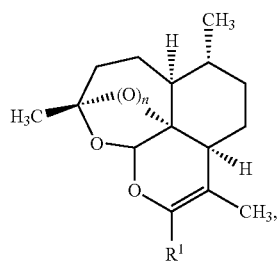

(II)

n is 2;
R$^1$ is —(CH$_2$)$_j$C(O)(CH$_2$)$_k$R$^2$;
j and k are each independently 0;
R$^2$ is independently substituted alkyl, unsubstituted $C_1$-$C_3$ alkyl, substituted or unsubstituted cycloalkyl, perfluoroalkyl, substituted or unsubstituted heteroalkyl, substituted or unsubstituted heterocycloalkyl, substituted aryl, substituted or unsubstituted arylalkyl, substituted or unsubstituted heteroaryl, substituted or unsubstituted heteroarylalkyl, substituted or unsubstituted (aryl or heteroaryl)-X-(aryl or heteroaryl) wherein X is O, S, NH or N($C_1$-$C_6$)alkyl, or a substituted or unsubstituted monosaccharide, and wherein each R$^2$ is optionally independently substituted with 1 to 5 R$^{10}$ groups.

* * * * *